(12) United States Patent
Kim et al.

(10) Patent No.: US 10,610,602 B2
(45) Date of Patent: Apr. 7, 2020

(54) TUMOR CELL-SPECIFIC RESPONSIVE SELF-ASSEMBLING DRUG NANOCONJUGATE

(71) Applicant: KOREA INSTITUTE OF SCIENCE AND TECHNOLOGY, Seoul (KR)

(72) Inventors: Kwangmeyung Kim, Seoul (KR); Ick Chan Kwon, Seoul (KR); Juho Park, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/925,830

(22) Filed: Mar. 20, 2018

(65) Prior Publication Data

US 2019/0083637 A1  Mar. 21, 2019

(30) Foreign Application Priority Data

Sep. 20, 2017 (KR) ........................ 10-2017-0121169

(51) Int. Cl.
| | | |
|---|---|---|
| A61K 47/64 | (2017.01) | |
| A61K 47/69 | (2017.01) | |
| A61K 47/65 | (2017.01) | |
| A61K 9/51 | (2006.01) | |
| A61K 31/704 | (2006.01) | |

(52) U.S. Cl.
CPC ............... *A61K 47/64* (2017.08); *A61K 9/51* (2013.01); *A61K 31/704* (2013.01); *A61K 47/65* (2017.08); *A61K 47/6929* (2017.08)

(58) Field of Classification Search
CPC .................................................. A61K 47/64
See application file for complete search history.

(56) References Cited

U.S. PATENT DOCUMENTS

| | | | | |
|---|---|---|---|---|
| 2005/0261188 | A1* | 11/2005 | Abad ................... | C07K 14/325 435/219 |
| 2006/0275775 | A1* | 12/2006 | Weissleder ........... | A61B 5/0071 435/6.12 |
| 2010/0189657 | A1* | 7/2010 | Weissleder ......... | A61K 49/0032 514/1.1 |
| 2011/0293728 | A1* | 12/2011 | Choi ................... | A61K 49/0017 424/491 |
| 2015/0259431 | A1* | 9/2015 | Stemmer .............. | C07K 14/535 424/85.7 |

FOREIGN PATENT DOCUMENTS

| | | |
|---|---|---|
| KR | 10-2003-0096356 A | 12/2003 |
| WO | WO 2004/046169 A2 | 6/2004 |

OTHER PUBLICATIONS

Lee et al., 2015, Enzyme-responsive doxorubicin release from dendrimer nanoparticles for anticancer drug delivery, International Journal of Nanomedicine, 10: 5489-5503.*
Kulsharova et al., 2013, In Vitro and In Vivo Imaging of Peptide-Encapsulated Polymer Nanoparticles for Cancer Biomarker Activated Drug Delivery, IEEE Trans Nanobioscience, 12(4): 304-310.*
Zhang et al., 2016, Design, Synthesis, and Biological Evaluation of New Cathepsin B-Sensitive Camptothecin Nanoparticles Equipped with a Novel Multifunctional Linker, Bioconjugate Chemistry, 27: 1267-1275.*
Shim et al., 2016, Cathepsin B-Specific Metabolic Precursor for In Vivo Tumor-Specific Fluorescence Imaging, Angew Chem Int Ed, 55: 14698-14703.*
Kolhatkar et al., 2015, Dendritic hexadecapeptide as a cathepsin B degradable carrier for delivery of HSP90 inhibitor, Bioorganic & Medicinal Chemistry Letters, 25: 3744-3747.*
Collins et al., 2010, Self-Assembly of Peptides into Spherical Nanoparticles for Delivery of Hydrophilic Moieties to the Cytosol, ACSNano, 4(5): 2856-2864.*
Samuel Janssen et al., "Screening a combinatorial peptide library to develop a human glandular kallikrein 2-activated prodrug as targeted therapy for prostate cancer", Molecular Cancer Therapeutics, Nov. 2004, pp. 1439-1450, vol. 3, No. 11.
Wang Ma et al., "Synergistic antitumor activity of a self-assembling camptothecin and capecitabine hybrid prodrug for improved efficacy", Journal of Controlled Release, 2017, pp. 102-111, vol. 263.
Zhipeng Chen et al., "Controlled release of free doxorubicin from peptide-drug conjugates by drug loading", Journal of Controlled Release, 2014, pp. 123-130, vol. 191.
Yin-Jia Cheng et al., "Self-assembled micelles of multi-functional amphiphilic fusion (MFAF) peptide for targeted cancer therapy", Polymer Chemistry, 2015, pp. 1-9.

* cited by examiner

*Primary Examiner* — Amber D Steele
(74) *Attorney, Agent, or Firm* — Foley & Lardner LLP

(57) ABSTRACT

Disclosed is a drug conjugate as a prodrug that is degraded by cathepsin B specifically expressed in tumor tissues to release doxorubicin. The drug conjugate can form self-assembled nanoparticles. In addition, the drug conjugate specifically responds to and is activated in tumor cells. Therefore, the use of the drug conjugate eliminates the incidence of side effects (for example, cell damage and apoptosis) during the course of cancer prevention or treatment.

5 Claims, 30 Drawing Sheets

Specification includes a Sequence Listing.

FRRG-DOX: SEQ ID NO: 7

SEQUENCE LISTING

```
<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug

<400> SEQUENCE: 1

Phe Arg Arg Gly
1

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug

<400> SEQUENCE: 2

Gly Gly Gly Gly Phe Arg Arg Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug

<400> SEQUENCE: 3

Gly Gly Phe Arg Arg Gly Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug

<400> SEQUENCE: 4

Phe Arg Arg Gly Gly Gly Gly Gly
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug
```

```
<400> SEQUENCE: 5

Arg Arg Gly
1

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug

<400> SEQUENCE: 6

Phe Arg Arg
1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug
<220> FEATURE:
<221> NAME/KEY: MOD_RES
<222> LOCATION: (5)..(5)
<223> OTHER INFORMATION: Doxorubicin

<400> SEQUENCE: 7

Phe Arg Arg Gly Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug
<220> FEATURE:
<221> NAME/KEY: MOD_RES
<222> LOCATION: (9)..(9)
<223> OTHER INFORMATION: Doxorubicin

<400> SEQUENCE: 8

Gly Gly Gly Gly Phe Arg Arg Gly Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug
<220> FEATURE:
<221> NAME/KEY: MOD_RES
<222> LOCATION: (9)..(9)
<223> OTHER INFORMATION: Doxorubicin

<400> SEQUENCE: 9

Gly Gly Phe Arg Arg Gly Gly Gly Xaa
1               5

<210> SEQ ID NO 10
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      tumor-specific amphiphilic prodrug
<220> FEATURE:
<221> NAME/KEY: MOD_RES
<222> LOCATION: (9)..(9)
<223> OTHER INFORMATION: Doxorubicin

<400> SEQUENCE: 10

Phe Arg Arg Gly Gly Gly Gly Gly Xaa
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      tumor-specific amphiphilic prodrug
<220> FEATURE:
<221> NAME/KEY: MOD_RES
<222> LOCATION: (4)..(4)
<223> OTHER INFORMATION: Doxorubicin

<400> SEQUENCE: 11

Arg Arg Gly Xaa
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly
1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Gly
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala Ala
1

<210> SEQ ID NO 15
<211> LENGTH: 5
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 15

Ala Ala Ala Ala Ala
1               5
```

TUMOR CELL-SPECIFIC RESPONSIVE SELF-ASSEMBLING DRUG NANOCONJUGATE

CROSS-REFERENCE TO RELATED APPLICATIONS

This application claims priority under 35 U.S.C. § 119 to Korean Patent Application No. 10-2017-0121169 filed on Sep. 20, 2017 in the Korean Intellectual Property Office, the disclosure of which is incorporated herein by reference in its entirety.

SEQUENCE LISTING

The instant application contains a Sequence Listing which has been filed electronically in ASCII format and is hereby incorporated by reference in its entirety. Said ASCII copy, created on Nov. 8, 2019, is named 115518-0110_SL.txt and is 3,941 bytes in size.

BACKGROUND OF THE INVENTION

1. Field of the Invention

The present invention relates to a tumor cell-specific responsive drug conjugate, and more specifically to a novel nanostructure of drug conjugate having an enzyme specificity for tumor cells that is selectively degraded by an enzyme present in tumor cells.

2. Description of the Related Art

Cancer is the leading cause of death around the world. Many therapeutic agents for cancer have been developed for more than a decade. The developed cytotoxic therapeutic agents for cancer are very effective in inhibiting the growth of cancer cells or killing cancer cells but have the effects of inhibiting the growth of normal cells and killing normal cells, causing serious side effects.

In efforts to solve these problems, methods and therapeutic agents targeting tumor cell growth signaling, receptors, and genetic mutation have been developed by conjugating anticancer agents (e.g., doxorubicin, paclitaxel, and monomethyl auristatin E (MMAE)) to peptides or linkers specifically reacting with particular proteases such that the anticancer agents are prevented from acting on normal cells.

Nevertheless, in the case of a therapeutic agent for cancer in which a protease-specific peptide with a short amino acid sequence is conjugated with a drug, the peptide is impossible to design such that it targets a specific protease expressed in various tumor cells and accurately recognizes the target protease. Thus, the problems of toxicity to tumor cells as well as normal cells still arise.

A peptide targeting a specific protease suffers from difficulty in recognizing a wide range of tumor cells and tissues and is accumulated in limited tumor tissues corresponding to particular sites, thus being unsuitable for commercialization.

In order to solve the above-described problems while minimizing damage to normal cells, there is a need to develop novel therapeutic agents for cancer that can specifically recognize a wide range of tumor cells and tissues, including metastatic cancers, can be delivered to tumor sites, and ensure excellent prophylactic or therapeutic effects of drugs.

PRIOR ART DOCUMENTS

Patent Documents

Patent Document 1: Korean Patent Publication No. 2003-0096356

SUMMARY OF THE INVENTION

The present invention has been made in view of the above problems, and it is one object of the present invention to provide a drug conjugate and self-assembled nanoparticles capable of delivering a drug specifically into tumor cells.

It is a further object of the present invention to provide a pharmaceutical composition and a health functional food composition for preventing or treating cancer, each of which includes the drug conjugate or the self-assembled nanoparticles as active ingredients.

One aspect of the present invention provides a low molecular weight drug conjugate including a hydrophobic drug selectively activated by cathepsin B in tumor cells and spontaneously forming spherical nanoparticles in a solvent.

The drug conjugate may include an amphiphilic peptide represented by Formula 1:

$$[X_0]_n\text{-}X_1\text{-}X_2\text{-}X_3\text{-}X_4 \qquad (1)$$

wherein $X_0$, $X_1$, and $X_4$ are each independently selected from glycine (G), alanine (A), valine (V), leucine (L), isoleucine (I), methionine (M), proline (P), phenylalanine (F), and tryptophan (W), $X_2$ and $X_3$ are each independently selected from arginine (R), serine (S), threonine (T), tyrosine (Y), cysteine (C), asparagine (N), and glutamine (Q), and n is an integer from 0 to 5, and a hydrophobic drug conjugated to one terminus of the amphiphilic peptide and forms self-assembled nanoparticles.

In Formula 1, $X_1$ may be phenylalanine (F), and $X_2$ and $X_3$ may be identical to each other and may be selected from arginine (R), serine (S), and threonine (T).

In Formula 1, $X_1$ may be phenylalanine (F), $X_2$ and $X_3$ may be arginine (R), $X_0$ and $X_4$ may be selected from glycine (G), alanine (A), valine (V), leucine (L), phenylalanine (F), and tryptophan (W).

The amphiphilic peptide may have the sequence set forth in any one of SEQ ID NOS: 1 to 4.

The hydrophobic drug may be selected from the group consisting of taxol, bendamustine, busulfan, carmustine, chlorambucil, cyclophosphamide, dacarbazine, adriamycin, daunomycin, ifosfamide, melphalan, procarbazine, streptozocin, temozolomide, asparaginase, capecitabine, cytarabine, 5-fluorouracil, fludarabine, gemcitabine, methotrexate, pemetrexed, raltitrexed, actinomycin-D, bleomycin, daunorubicin, doxorubicin, pegylated liposomal doxorubicin, epirubicin, idarubicin, mitomycin, mitoxantrone, etoposide, docetaxel, irinotecan, paclitaxel, topotecan, vinblastine, vincristine, vinorelbine, carboplatin, cisplatin, oxaliplatin, alemtuzumab, BCG, bevacizumab, cetuximab, denosumab, erlotinib, gefitinib, imatinib, interferon, ipilimumab, lapatinib, panitumumab, rituximab, sunitinib, sorafenib, temsirolimus, trastuzumab, clodronate, ibandronic acid, pamidronate, and zoledronic acid.

The drug conjugate may have a molecular weight of 800 to 3000 Da.

The amphiphilic peptide may be degraded by cathepsin B present in tumor cells to release the hydrophobic drug.

A further aspect of the present invention provides spherical self-assembled nanoparticles that are spontaneously formed by the drug conjugate in a solvent and have a structure in which hydrophobic moieties of the drug conjugate form a core and hydrophilic moieties of the drug conjugate are exposed to the outside of the core.

The amphiphilic peptide of the drug conjugate may be degraded by cathepsin B present in tumor cells to release the hydrophobic drug located at the core of the nanoparticles.

The solvent may be selected from the group consisting of distilled water, phosphate buffered solution (PBS), physiological saline, distilled water containing 0.5 to 1% NaCl, and phosphate buffered solution (PBS) containing 0.5 to 1% NaCl.

The self-assembled nanoparticles may have an average diameter of 50 to 500 nm.

Another aspect of the present invention provides a pharmaceutical composition for preventing or treating cancer containing the drug conjugate or the self-assembled nanoparticles as active ingredients.

Yet another aspect of the present invention provides a health functional food composition for preventing or ameliorating cancer containing the drug conjugate or the self-assembled nanoparticles as active ingredients.

The drug conjugate of the present invention is a prodrug that is degraded by cathepsin B specifically expressed in tumor tissues to release doxorubicin. The drug conjugate of the present invention specifically responds to and is activated in tumor cells. Therefore, the use of the drug conjugate eliminates the incidence of side effects (for example, cell damage and apoptosis) during the course of cancer prevention or treatment.

In addition, the drug conjugate of the present invention is cleavable by cathepsin B, consists of a hydrophilic peptide (Arg-Arg, RR), hydrophobic amino acids phenylalanine (Phe, F) and glycine (Gly, G), and doxorubicin conjugated to the amphiphilic peptide, is stable without causing toxicity to normal cells because it forms stable nanoparticles in an aqueous state, and has a specific prophylactic or therapeutic effect on tumor cells.

Furthermore, the drug conjugate and the self-assembled nanoparticles of the present invention can solve the problems of toxicity and tumor-specific activity encountered with conventional therapeutic agents for cancer. Moreover, the drug conjugate and the self-assembled nanoparticles of the present invention are accumulated in tumor cells without the need to use carriers, vehicles, and nanocarriers.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1A:
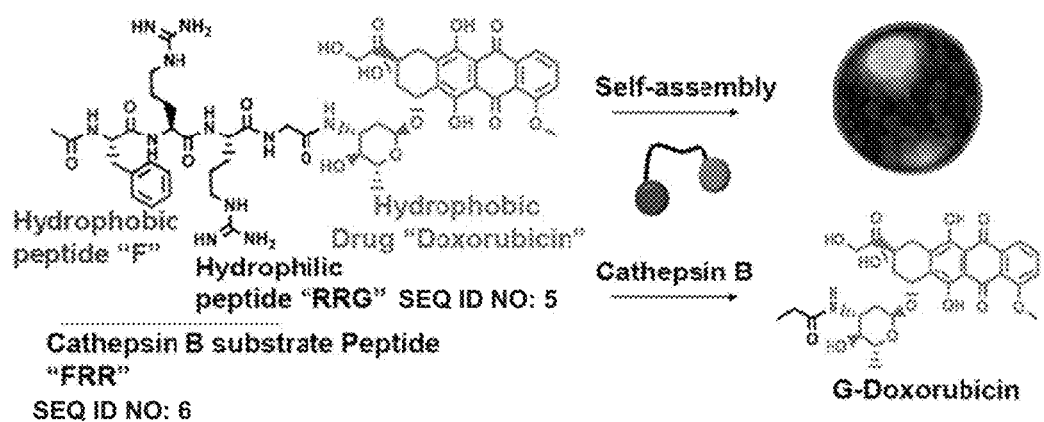
FIG. 1A shows a procedure for synthesizing FRRG-DOX (SEQ ID NO: 7) with a molecular weight as low as ~1100 Da without using any synthetic linker in which doxorubicin is conjugated to an acylated peptide (FRRG (SEQ ID NO: 1)) by a one-step process after a solid-phase synthesis technique.

Several aspects and various embodiments of the present invention will now be described in more detail.

As used herein, the term "peptide" refers to a linear molecule in which amino acid residues bind to each other via a peptide linkage.

For reference, representative amino acids and their abbreviations are as follows: alanine (Ala, A), isoleucine (Ile, I), leucine (Leu, L), methionine (Met, M), phenylalanine (Phe, F), proline (Pro, P), tryptophan (Trp, W), valine (Val, V), asparagine (Asn, N), cysteine (Cys, C), glutamine (Gln, Q), glycine (Gly, G), serine (Ser, S), threonine (Thr, T), tyrosine (Try, Y), aspartic acid (Asp, D), glutamic acid (Glu, E), arginine (Arg, R), histidine (His, H), and lysine (Lys, K).

The most important consideration in preparing a drug conjugate of the present invention is the interaction or relationship between an amphiphilic peptide specifically degraded by cathepsin B and a hydrophobic drug. That is, all peptides specifically degraded by cathepsin B are not efficiently conjugated with hydrophobic drugs, hydrophobic drugs released from peptides specifically degraded by cathepsin B do not always maintain their good effects on tumor cells, or drug conjugates cannot ensure desired effects (e.g., high biostability).

Considering this interaction between an amphiphilic peptide and a hydrophobic drug, the present inventors have specially designed an amphiphilic peptide specifically degraded by cathepsin B, modified a linker ($[X_4]$) through which the amphiphilic peptide can be effectively conjugated with a hydrophobic drug, and finally arrived at the present invention.

One aspect of the present invention provides a drug conjugate including an amphiphilic peptide represented by Formula 1:

$$[X_0]_n\text{-}X_1\text{-}X_2\text{-}X_3\text{-}X_4 \qquad (1)$$

wherein $X_0$, $X_1$, and $X_4$ are each independently selected from glycine (G), alanine (A), valine (V), leucine (L), isoleucine (I), methionine (M), proline (P), phenylalanine (F), and tryptophan (W), $X_2$ and $X_3$ are each independently selected from arginine (R), serine (S), threonine (T), tyrosine (Y), cysteine (C), asparagine (N), and glutamine (Q), and n is an integer from 0 to 5, and a hydrophobic drug conjugated to one terminus of the amphiphilic peptide.

In Formula 1, $X_4$ may be a single amino acid or a peptide consisting of one or more repeated amino acids, for example, G, GG, GGG, GGGG (SEQ ID NO: 12), GGGGG (SEQ ID NO: 13), A, AA, AAA, AAAA (SEQ ID NO: 14) or AAAAA (SEQ ID NO: 15).

Thus, Formula 1 may be represented by $[X_0]_n$-$X_1$-$X_2$-$X_3$-$[X_4]_m$ (wherein n is an integer from 0 to 5 and m is an integer from 1 to 5).

In the drug conjugate of the present invention, the amphiphilic peptide consists of hydrophilic amino acids ($X_2$ and $X_3$) and hydrophobic amino acids ($X_0$, $X_1$, and $X_4$) bound to each other via a peptide linkage. The drug conjugate is prepared by conjugating the hydrophobic amino acids ($X_0$, $X_1$, and $X_4$) of the amphiphilic peptide with the hydrophobic drug, does not undergo nonenzymatic hydrolysis in aqueous and powder forms due to its stability against hydrolysis, and is very structurally stable.

The amphiphilic peptide is prepared by the series of processes shown in FIG. 1A. The amphiphilic peptide may be prepared by any suitable chemical synthesis method known in the art, particularly a solid-phase synthesis technique (Merrifield, J. Amer. Chem. Soc. 85:2149-54(1963); Stewart, et al., Solid Phase Peptide Synthesis, 2nd. ed., Pierce Chem. Co.: Rockford, 111(1984)). There is no particular restriction on the method for synthesizing the amphiphilic peptide. Preferably, the amphiphilic peptide is prepared by a solid-phase peptide synthesis (SSPS) method in which Fmoc-protected amino acid monomers are sequentially attached to a Rink amide resin with C-terminal amide groups.

Preferably, the chemical stability of the amphiphilic peptide is enhanced by acetylating the N-terminal amino group and amidating the C-terminus.

In the preparation of the amphiphilic peptide, amine protecting groups may be used to protect the nitrogen atoms of the amine groups of the amphiphilic peptide. Suitable amine protecting groups known in the art may be used without limitation and examples thereof include methyloxycarbonyl, benzyloxycarbonyl, p-methoxybenzyloxycarbonyl, t-butyloxycarbonyl (Boc), 9-fluorenylmethyloxycarbonyl (FMOC), allyloxycarbonyl (Alloc), benzoyl (Bz), benzyl (Bn), p-methoxybenzyl (PMB), 3,4-dimethoxybenzyl (DMPM), p-methoxyphenyl (PMP), tosyl (Ts), trimethylsilylethyloxycarbonyl (Teoc), benzhydryl, triphenylmethyl (Trityl), (4-methoxyphenyl)diphenylmethyl (Mmt), dimethoxytrityl (DMT), and diphenylphosphino groups.

In the drug conjugate of the present invention, the hydrophobic drug is conjugated to the amphiphilic peptide. The interaction between the amphiphilic peptide and the hydrophobic drug stabilizes the drug conjugate to protect normal cells from the toxicity of the drug. This stabilization markedly improves the in vivo structural stability and solubility of the drug conjugate while overcoming and solving the problems of side effects encountered with conventional therapeutic agents for cancer.

That is, the drug conjugate of the present invention is substantially free from toxicity to normal cells, which is a problem of conventional therapeutic agents for cancer, and has an enhanced therapeutic effect on cancer. The drug conjugate of the present invention uses doxorubicin as the hydrophobic drug. The single use of doxorubicin causes damage to or apoptosis of heart tissues and even other organ tissues. In contrast, the drug conjugate of the present invention considerably reduces the toxicity of the drug to normal cells and has a prophylactic or therapeutic effect on tumor tissues, which were demonstrated through numerous experimental examples that follow.

Due to its high solubility in physiological solutions, the drug conjugate of the present invention is easily absorbed, achieving high bioavailability. In addition, the drug conjugate of the present invention has improved stability and specificity for tumor cells and is thus effective in preventing or treating cancer.

The amphiphilic peptide of the drug conjugate according to the present invention is degraded by cathepsin B present in tumor cells. As a result, the hydrophobic drug is released in the form of G-DOX and absorbed and delivered into tumor cells to inhibit growth and metastasis of the tumor tissues. The other small peptide molecules are degraded into non-toxic smaller molecules, which participate in in vivo metabolism or are released ex vivo through the kidneys. For these reasons, the drug conjugate of the present invention is highly biocompatible.

The drug conjugate of the present invention, in which the amphiphilic peptide represented by Formula 1 and the hydrophobic drug are conjugated to each other, self-assembles into more stable nanoparticles in aqueous solutions and physiological solutions. As a result of this self-assembly, the drug is specifically activated in tumor cells. For these reasons, the drug conjugate of the present invention is very therapeutically effective.

Cathepsin B is specifically expressed in tumor cells, particularly in metastatic cancer, and its expression in normal cells is limited. Accordingly, the cathepsin B-targeting drug conjugate of the present invention is effective in preventing or treating cancer, most preferably metastatic cancer.

Since cathepsin B is not substantially secreted in vitro, there is a very low possibility that cathepsin B may be false positive in normal cells other than tumor cells and in normal tissues other than tumor tissues. In contrast, in the case where a drug conjugate targets a protease other than cathepsin B, a peptide for detecting the corresponding protease is difficult to design and the therapeutic effect of the drug conjugate specific only for the particular site is limited to a particular cancer disease such as prostate cancer and is not extended to metastatic cancer. Further, the protease may be secreted in vitro, causing false positivity.

In Formula 1, preferably, $X_1$ is phenylalanine (F) and $X_2$ and $X_3$ are identical to each other and are selected from arginine (R), serine (S), and threonine (T).

In Formula 1, more preferably, $X_1$ is phenylalanine (F), $X_2$ and $X_3$ are arginine (R), and $X_0$ and $X_4$ are selected from glycine (G), alanine (A), valine (V), leucine (L), phenylalanine (F), and tryptophan (W). When the amphiphilic peptide is represented by $[X_0]_n$F-R-R-$[X_4]_m$ (n=0-5, m=1-5), it has the highest specificity for tumor cells without affecting normal cells. That is, it is most preferred that the sequence F-R-R (SEQ ID NO: 6) is fixed in the amphiphilic peptide. In this case, the amphiphilic peptide forms nanoparticles whose size varies depending on the amino acid residues bound to one (e.g., right) or both termini of the peptide F-R-R (SEQ ID NO: 6). The efficacy of the drug conjugate is also determined by the terminal amino acid residues, which was demonstrated through the experimental examples that follow.

Specifically, when compared to a drug conjugate using an amphiphilic peptide in which $X_1$ is deleted or altered, the drug conjugate of the present invention is highly specific for tumor cells and has a significantly enhanced synergistic prophylactic or therapeutic effect of the drug in activated tumor cells.

$X_0$ in Formula 1 serves to improve the flexibility of the drug conjugate in which the amphiphilic peptide is conjugated with the hydrophobic drug. $X_0$ is not especially limited so long as it does not affect the activity of the hydrophobic drug in tumor cells. $X_0$ is preferably selected from glycine (G), alanine (A), valine (V), leucine (L), phenylalanine (F), and tryptophan (W). $X_0$ is most preferably glycine (G). $X_0$ may be absent in the amphiphilic peptide, but even if present, the drug conjugate can sufficiently perform its role (n is from 0 to 5). The drug conjugate flows stably in an in vivo physiological environment, ensuring specificity for tumor cells, which were demonstrated through the experimental examples that follow.

$X_4$ acts as a linker through which the amphiphilic peptide is conjugated with the hydrophobic drug. $X_4$ maintains a stable conjugated state of the drug conjugate in an in vivo physiological environment. When the amphiphilic peptide is degraded by cathepsin B, $X_4$ allows the hydrophobic drug separated from the amphiphilic peptide to be released intact. Accordingly, the linker $X_4$ is not specially limited so long as it does not affect the activity of the hydrophobic drug in tumor cells. $X_4$ is preferably selected from glycine (G), alanine (A), valine (V), leucine (L), phenylalanine (F), and tryptophan (W) and is most preferably glycine (G). The binding number (m) of $X_4$ is not specially limited but is preferably 1. When the binding number of $X_4$ is 1 or greater, two or more glycine (G) residues are bound to the hydrophobic drug degraded by cathepsin B, weakening the pharmacological effects of the hydrophobic drug in cells.

According to an embodiment of the present invention, the drug conjugate of the present invention is most effective in achieving stability, biocompatibility, specific activity against tumor cells, biocompatibility with normal cells, inhibited side effects, and prophylactic or therapeutic effect of the drug when the amphiphilic peptide has the sequence set forth in any one of SEQ ID NOS: 1 to 4:

| | |
|---|---|
| FRRG | (1) |
| GGGGFRRG | (2) |
| GGFRRGGG | (3) |
| FRRGGGG | (4) |

The hydrophobic drug may be selected from the group consisting of taxol, bendamustine, busulfan, carmustine, chlorambucil, cyclophosphamide, dacarbazine, adriamycin, daunomycin, ifosfamide, melphalan, procarbazine, streptozocin, temozolomide, asparaginase, capecitabine, cytarabine, 5-fluorouracil, fludarabine, gemcitabine, methotrexate, pemetrexed, raltitrexed, actinomycin-D, bleomycin, daunorubicin, doxorubicin, pegylated liposomal doxorubicin, epirubicin, idarubicin, mitomycin, mitoxantrone, etoposide, docetaxel, irinotecan, paclitaxel, topotecan, vinblastine, vincristine, vinorelbine, carboplatin, cisplatin, oxaliplatin, alemtuzumab, BCG, bevacizumab, cetuximab, denosumab, erlotinib, gefitinib, imatinib, interferon, ipilimumab, lapatinib, panitumumab, rituximab, sunitinib, sorafenib, temsirolimus, trastuzumab, clodronate, ibandronic acid, pamidronate, and zoledronic acid.

The molecular weight of the drug conjugate is preferably in the range of 800 to 3000 Da. Outside this range, there is a limitation in forming self-assembled nanoparticles in an aqueous state. Even when formed, the self-assembled nanoparticles increase excessively in size, suffering from difficulty in entering cells.

The drug conjugate of the present invention can be prepared by a simple one-step process for conjugating the hydrophobic drug to the low molecular weight amphiphilic peptide. In contrast, a conventional drug conjugate having a high molecular weight, like a macromolecule or polymer, is synthesized by a complicated process under difficult-to-control conditions at high cost. Further, the proportion of a drug loaded in or bound to the conventional drug conjugate is lowered (<5%), leading to unsatisfactory clinical results. Moreover, an excess of the drug needs to be administered for desired clinical results, leading to increased side effects caused by toxicity to normal cells.

The drug conjugate of the present invention can be prepared in very high yield through a simple synthesis method without the need to introduce any additional process. In addition, the low molecular weight drug conjugate of the present invention reacts with an enzyme present in tumor cells to release the drug. Due to these advantages, the drug conjugate of the present invention is more effective in treating cancer than conventional therapeutic agents for cancer.

As described previously, when the drug conjugate of the present invention is administered in vivo, the amphiphilic peptide is not cleaved in normal cells or tissues. As a result, the hydrophobic drug is not activated and is not exposed to the surface of normal cells. In contrast, the amphiphilic peptide and the hydrophobic drug or some amino acids of the amphiphilic peptide and the hydrophobic drug are cleaved in tumor cells or tissues by cathepsin B expressed in the cells. The cleaved hydrophobic drug is accumulated and activated in tumor cells, achieving specific prophylactic or therapeutic effects on tumor cells (see FIG. 1A).

A further aspect of the present invention provides spherical self-assembled nanoparticles that are spontaneously formed by the drug conjugate in a solvent and have a structure in which the hydrophobic moieties of the drug conjugate form a core and the hydrophilic moieties of the drug conjugate are exposed to the outside of the core.

The binding between the drug conjugate molecules makes the self-assembled nanoparticles stable and spherical, effectively enhances the stability of the drug, increases the specific response of the self-assembled nanoparticles to tumor cells, and enables oral or parenteral application of the self-assembled nanoparticles.

The self-assembled nanoparticles are formed by aggregation and self-assembly of the drug conjugate when the amphiphilic drug conjugate is dissolved in water, as shown in FIG. 1A.

Specifically, the nanoparticle shown in FIG. 1A is spherical and consists of inner and outer membranes formed by the drug conjugate molecules connected to each other. The outer membrane of the nanoparticle refers to a shell formed by the hydrophilic peptides RRG of the drug conjugate connected to one another and the inner membrane of the nanoparticle refers to a core formed by the hydrophobic amino acid (F) and the hydrophobic drug of the drug conjugate connected to one another.

The drug conjugate constituting the self-assembled nanoparticles plays an important role in specifically recognizing tumor tissues or cells. The drug conjugate consists of the amphiphilic peptide and the hydrophobic drug having an anticancer effect. The structure of the drug conjugate is the same as that described above and a description thereof is omitted to avoid duplicate.

The amphiphilic peptide of the drug conjugate is degraded by cathepsin B present in tumor cells to release the hydrophobic drug located at the core of the nanoparticles.

The solvent may be selected from the group consisting of distilled water, phosphate buffered solution, physiological saline, distilled water containing 0.5 to 1% NaCl, and phosphate buffered solution (PBS) containing 0.5 to 1% NaCl.

The average diameter of the self-assembled nanoparticles is preferably in the range of 50 to 500 nm. Out of this range, the self-assembled nanoparticles suffer from difficulty in entering cells, failing to exert a prophylactic or therapeutic effect.

Another aspect of the present invention provides a pharmaceutical composition for preventing or treating cancer including the drug conjugate or the self-assembled nanoparticles as active ingredients.

The content of the drug conjugate or the self-assembled nanoparticles in the pharmaceutical composition of the present invention may be appropriately adjusted depending on various factors such as the symptom and progression of the disease and the condition of the patient. The drug conjugate or the self-assembled nanoparticles are present in an amount of 30 to 80% by weight, preferably 50 to 70% by weight, based on the total weight of the composition, but is not limited thereto.

The drug conjugate or the self-assembled nanoparticles as active ingredients may be formulated with pharmaceutically acceptable carriers, diluents or excipients.

The pharmaceutical composition of the present invention can be formulated into oral preparations, such as powders, granules, tablets, capsules, suspensions, emulsions, syrups, and aerosols, and other preparations, such as external preparations, suppositories, and sterile injectable solutions, according to a conventional method suitable for each preparation.

Examples of carriers, excipients, and diluents suitable for the formulation of the pharmaceutical composition according to the present invention include, but are not limited to, lactose, dextrose, sucrose, sorbitol, mannitol, xylitol, erythritol, maltitol, starch, acacia rubber, alginate, gelatin, calcium phosphate, calcium silicate, cellulose, microcrystalline cellulose, polyvinyl pyrrolidone, methylhydroxybenzoate, propylhydroxybenzoate, water, talc, magnesium stearate, and mineral oil.

The pharmaceutical composition of the present invention may further include one or more pharmaceutically acceptable additives selected from diluents and excipients commonly used in the art, such as fillers, extenders, binders, wetting agents, disintegrating agents, and surfactants.

The pharmaceutical composition of the present invention can be formulated into solid preparations for oral administration, such as tablets, pills, powders, granules, and capsules. Such solid preparations may be prepared by mixing at least one excipient, for example, starch, sucrose, lactose, gelatin or calcium carbonate, with the drug conjugate or the self-assembled nanoparticles.

The pharmaceutical composition of the present invention can be formulated into liquid formulations for oral administration, such as suspensions, liquids for internal use, syrups, and emulsions. Such liquid formulations may include simple diluents commonly used in the art, for example, water and liquid paraffin, and various types of excipients, for example, wetting agents, sweetening agents, fragrances and preservatives.

The pharmaceutical composition of the present invention can be formulated into preparations for parenteral administration. Examples of such preparations for parenteral administration include sterile aqueous solutions, non-aqueous solvents, emulsions, suspensions, freeze-drying agents, and suppositories. The non-aqueous solvents and the suspensions may be propylene glycol, polyethylene glycol, vegetable oils such as olive oil, and injectable esters such as ethyl oleate. Witepsol, Tween 61, laurin fat, and glycerogelatin may be used as bases of the suppositories.

A preferred dose of the pharmaceutical composition according to the present invention depends on the condition and body weight of the patient, the severity of the disease, the form of the drug, and the route and time of administration but can be appropriately selected by one skilled in the art. For desired effects, the drug conjugate or the self-assembled nanoparticles as active ingredients are administered in an amount of 0.0001 mg/kg to 100 mg/kg, preferably 0.001 mg/kg to 60 mg/kg for an adult. The pharmaceutical composition of the present invention may be administered in single or divided doses per day. The dose of the pharmaceutical composition according to the present invention may be appropriately increased or reduced taking into consideration the age, sex, body weight, diet, and rate of excretion of the patient, and other drugs that are currently taken. The pharmaceutical composition of the present invention is prepared taking into consideration the effective amount of the active ingredients. The pharmaceutical composition of the present invention may be provided in a unit dosage form. If necessary, the unit dosage form may be administered using a specialized dosage regimen according to the judgement of specialists who supervise or observe the administration of drug and individual request. Alternatively, the unit dosage form may be administered in divided doses at regular time intervals.

The pharmaceutical composition of the present invention may be administered to mammals, such as rats, mice, livestock, and humans, via various routes, for example, orally or by intraperitoneal, intrarectal, intravenous, intramuscular, subcutaneous or intrauterine or intracerebrovascular injection.

The pharmaceutical composition of the present invention is effective in preventing or treating general cancer diseases, including solid tumors and blood born tumors. Non-limiting examples of such cancer diseases include breast cancer, ovarian cancer, placenta cancer, stomach cancer, colon cancer, lung cancer, non-small cell lung cancer, bone cancer, head or neck cancer, skin or ocular malignant melanoma, uterine cancer, colorectal cancer, small bowel cancer, rectal cancer, cancer around anal, fallopian tubal cancer, endometrial carcinoma, cervical carcinoma, vaginal carcinoma, vulvar carcinoma, Hodgkin's disease, esophagus cancer, lymphoma cancer, bladder cancer, gallbladder cancer, endocrine cancer, thyroid cancer, parathyroid cancer, adrenal cancer, soft tissue sarcoma, urethra cancer, penis cancer, prostate cancer, acute or chronic leukemia, lymphocytic lymphoma, kidney or ureter cancer, kidney cell cancer, kidney pelvis carcinoma, central nervous system (CNS) tumor, primary CNS lymphoma, spinal cord tumor, brainstem glioma, pituitary adenoma, and fibrosarcoma.

Therefore, the present invention provides use of the pharmaceutical composition for preventing or treating the above-described diseases, use of the drug conjugate or the self-assembled nanoparticles for preparing a medicament for preventing or treating the above-described diseases, and a method for preventing or treating the above-described diseases including administering a pharmaceutically acceptable amount of the drug conjugate or the self-assembled nanoparticles to a mammal, including a human.

In the method for preventing or treating cancer according to the present invention, the pharmaceutical composition may be administered via a general route of administration due to its high specificity for tumor cells. The route of administration is not limited so long as the pharmaceutical composition can reach a target tissue. The pharmaceutical composition of the present invention may be administered intraperitoneally, intravenously, intramuscularly, subcutaneously, intradermally, orally, intranasally, intrapulmonarily or intrarectally according to its purpose of use. However, the route of the administration of the pharmaceutical composition is not particularly limited.

The drug conjugate or the self-assembled nanoparticles may be added to a food or beverage for the purpose of preventing or ameliorating cancer.

When the drug conjugate or the self-assembled nanoparticles are used as food additives, they may be added without further processing or may be optionally used together with other foods or food ingredients in accordance with methods known in the art. The amount of the active ingredients can be suitably determined according to their purpose of use (such as prophylactic, health care or therapeutic purpose). When it is intended to produce a food or beverage, the drug conjugate or the self-assembled nanoparticles are typically added in an amount of 15 parts by weight or less, preferably 10 parts by weight or less, based on 100 parts by weight of the raw materials of the food or beverage. In the case where the food or beverage is taken for a long time for the purpose of health and hygiene or health care, the amount of the active ingredients may be adjusted to less than the lower limit defined above. The active ingredients may also be used in an amount exceeding the upper limit defined above because they are free from problems associated with safety.

There is no particular restriction on the kind of the food. Examples of foods containing the drug conjugate or the self-assembled nanoparticles include meats, sausages, breads, chocolates, candies, snacks, crackers, cookies, pizza, flour products (e.g., instant noodles), chewing gums, dairy products (including ice creams), soups, beverages, teas, drinks, alcoholic drinks, and vitamin complexes. The food is intended to include health functional foods in a broad aspect.

A health functional beverage composition of the present invention may further include various flavoring agents or natural carbohydrates, like general beverages. For example, the natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. The health functional beverage composition may further include natural or synthetic sweetening agents. The natural sweetening agents include thaumatin and stevia extracts. The synthetic sweetening agents include saccharin and aspartame.

The health functional food composition of the present invention may further include a variety of nutrients, vitamins, minerals (electrolytes), synthetic and natural flavors, coloring agents, fillers (cheese and chocolates), pectic acid and its salts, alginic acid and its salts, organic acids, protective colloidal thickeners, pH adjusting agents, stabilizers, preservatives, glycerin, alcohols, and carbonating agent for carbonated beverages.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

The experimental results of the following examples, including comparative examples, are merely representative and the effects of the exemplary embodiments of the present invention that are not explicitly presented hereinafter can be specifically found in the corresponding sections Statistics Differences between experimental and control groups were analyzed using one-way ANOVA and were considered statistically significant (shown in asterisks (*) in the figures).

Examples 1-4: Synthesis of Drug Conjugates FRRG-DOX (SEQ ID NO: 7), GGGGFRRG-DOX (SEQ ID NO: 8), GGFRRGGG-DOX (SEQ ID NO: 9), and Frrggggg-Dox (Seq Id No: 10)

Trt-Cl Resin and all Fmoc amino acids were purchased from GL Biochem (Shanghai, China). Coupling reagents and cleavage cocktail reagents were purchased from Sigma Aldrich, and other solvents were purchased Daejung Chemical (Korea).

FRRG (SEQ ID NO: 1), GGGGFRRG (SEQ ID NO: 2), GGFRRGGG (SEQ ID NO: 3), FRRGGGGG (SEQ ID NO: 4), and RRG (SEQ ID NO: 5) were synthesized by Fmoc solid phase peptide synthesis (SPPS) using ASP48S (Peptron, Inc., Korea).

The peptides were purified by reverse-phase HPLC (Shimadzu prominence HPLC, Japan) using a Vydac Everest C18 column (250 mm×22 mm, 10 µm, USA). Elution was performed with a water-acetonitrile linear gradient (10-75% (v/v) of acetonitrile) containing 0.1% (v/v) trifluoroacetic acid. The molecular weights of the purified peptides were confirmed by LC/MS (Shimadzu LC/MS-2020 series, Japan). The purified peptides were lyophilized using FDT12012 (Operon, Korea).

1) Synthesis of Amphiphilic Peptides FRRG (SEQ ID NO: 1), GGGGFRRG (SEQ ID NO: 2), GGFRRGGG (SEQ ID NO: 3), and FRRGGGGG (SEQ ID NO: 4)

Each peptide was synthesized in accordance with a general solid state peptide synthesis protocol. The target amino acid sequences FRRG (SEQ ID NO: 1), GGGGFRRG (SEQ ID NO: 2), GGFRRGGG (SEQ ID NO: 3), and FRRGGGGG (SEQ ID NO: 4) were synthesized using a peptide synthesizer (ASP48S, Peptron, Inc., Korea). Fmoc was used as a standard amino acid protecting group for peptide synthesis.

Specifically, rocking was performed twice with DMF including 20% piperidine for 10 min to remove the Fmoc protecting group. Coupling was performed with Fmoc amino acid (8 eq.), HOBT (8 eq.), HBTU (8 eq.), and DIPEA (16 eq.) in DMF for 2 h. In each stage, the resin was washed with DMF and methanol (×2 each).

After the synthesis of each peptide having the designed sequence was completed, the crude peptide was separated from the resin by reaction with a TFA/EDT/Thioanisole/TIS/DW solution (90/2.5/2.5/2.5/2.5 Volume) for 2 h. The solution was precipitated with cold ether and pellets were collected by centrifugation. A powder was obtained by evaporation.

The crude peptide was dissolved in distilled water and purified by reverse-phase HPLC with a C18 column. Elution was performed with a water-acetonitrile linear gradient (10-75% (v/v) of acetonitrile) containing 0.1% (v/v) trifluoroacetic acid. The purified peptide was lyophilized and stored.

2) Synthesis of Drug Conjugates

Each of the amphiphilic peptides FRRG (SEQ ID NO: 1), GGGGFRRG (SEQ ID NO: 2), GGFRRGGG (SEQ ID NO:

3), and FRRGGGGG (SEQ ID NO: 4) prepared in 1) was dissolved in water, and doxorubicin was added thereto. The mixture was stirred at room temperature for 24 h. The resulting peptide structure was purified by reverse-phase HPLC (water-acetonitrile, 0.1% TFA).

Doxorubicin, the peptide FRRG, and the drug conjugate FRRG-DOX (SEQ ID NO: 7) were dissolved in DMSO-$d_6$ and their characteristic peaks were identified by 600 MHz $^1$H-NMR (DD 2600 MHz FT NMR, Agilent Technologies, USA) to analyze their chemical structures. The molecular weights of FRRG-DOX (SEQ ID NO: 7) and G-DOX (a peptide fragment cleaved from FRRG-DOX (SEQ ID NO: 7)) were analyzed by matrix-assisted laser desorption/ionization (MALDI, AB Sciex TOF/TOF 5800 System, USA) (with cyano-4-hydroycinnamic acid matrix).

3) Characterization

Figure 7:
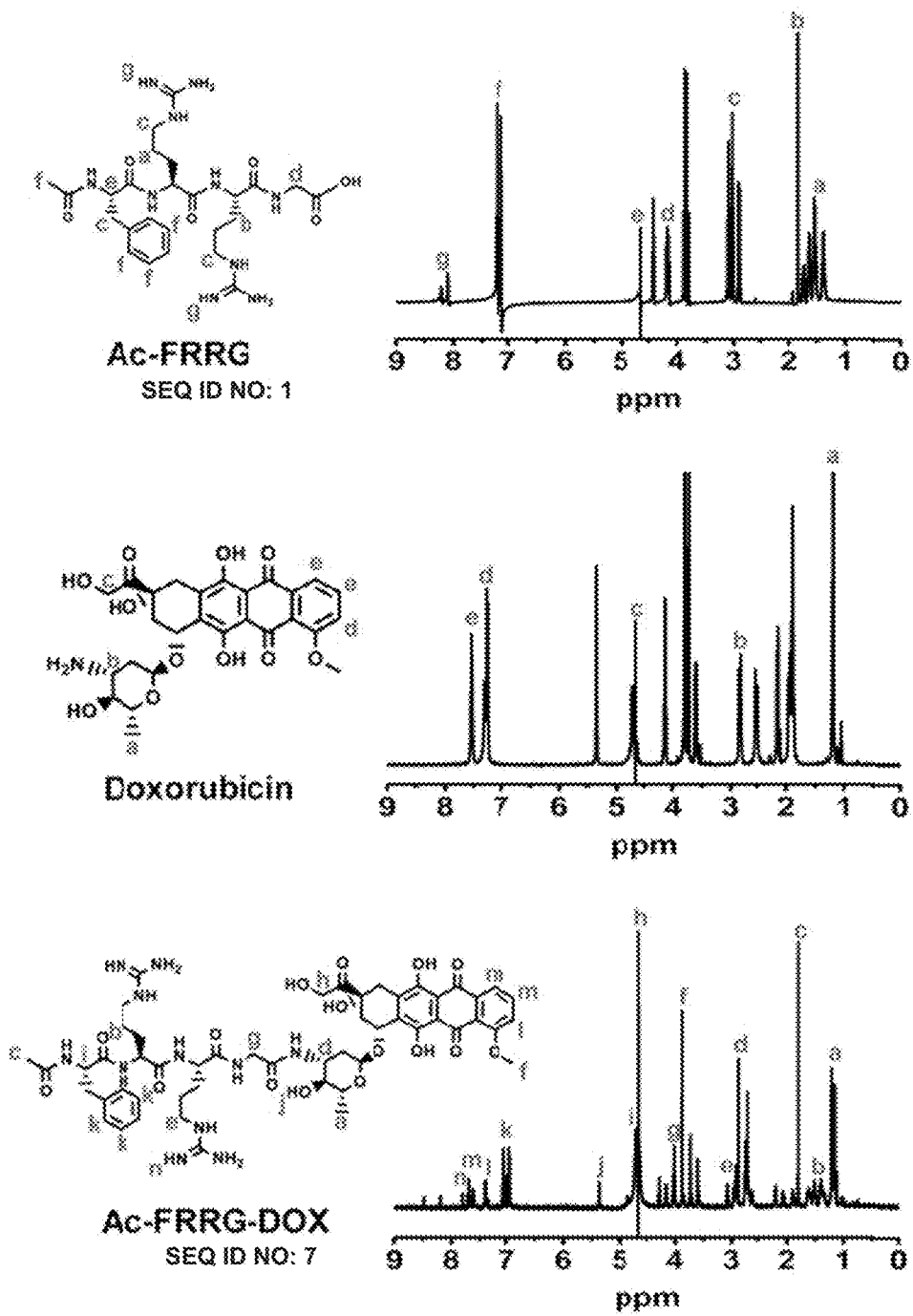
FIG. 7 shows a proton-NMR spectrum of FRRG-DOX (SEQ ID NO: 7) (Example 1)
Figure 8A:
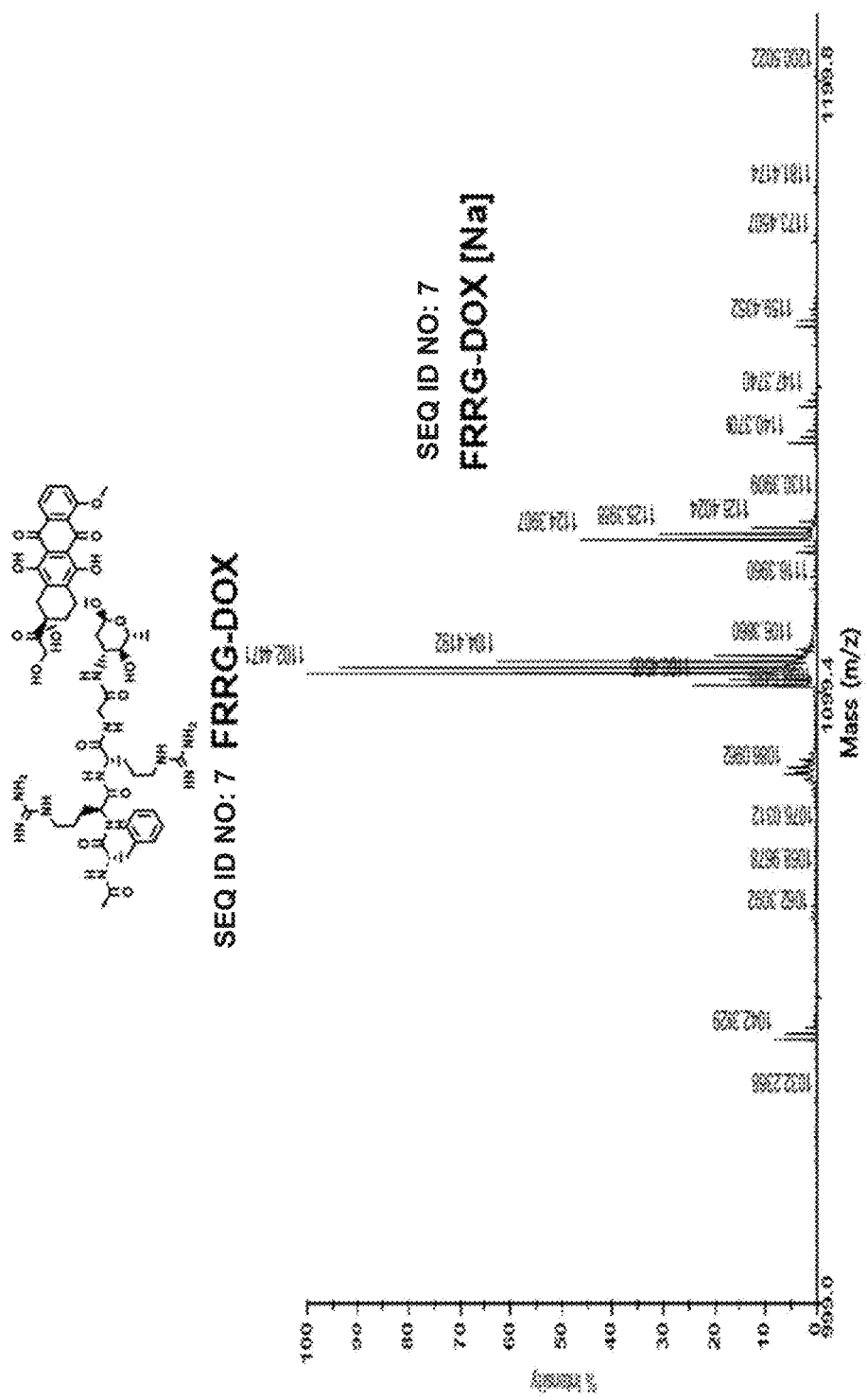
FIGS. 8A and 8B show MALDI-TOF spectra of FRRG-DOX (SEQ ID NO: 7) (Example 1) and G-DOX, respectively.
Figure 8B:
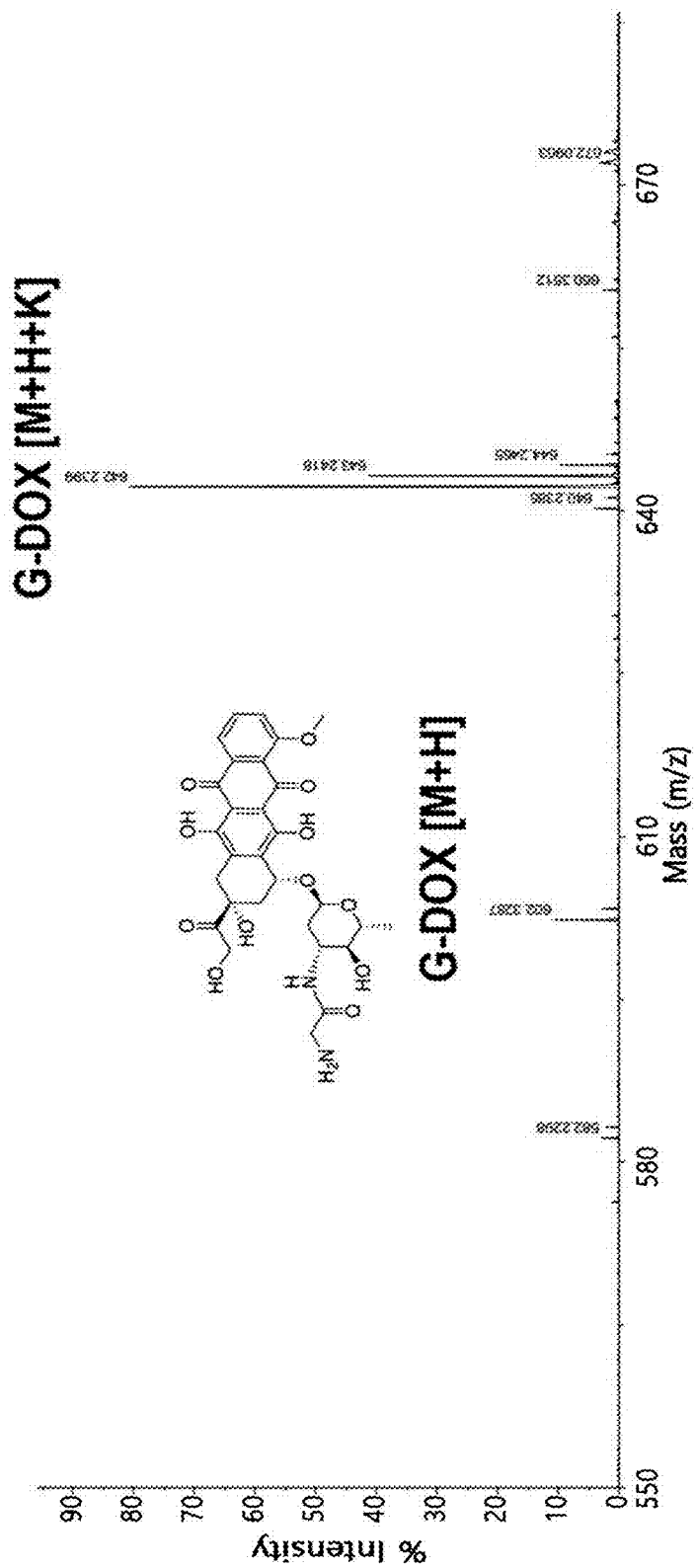

The drug conjugates or the amphiphilic peptides were characterized by NMR. As a result, peaks of doxorubicin and the amphiphilic peptides appeared at 1.1-1.8 ppm and 6.8-8.4 ppm (FIG. 7). The MALDI-TOF spectrum of FRRG-DOX (SEQ ID NO: 7) yielded the following results: m/z calcd.: 1101.5, found: 1102.4[M+H+] (FIG. 8A). The MALDI-TOF spectrum of G-DOX, a cleavage product of FRRG-DOX (SEQ ID NO: 7) by cathepsin B, yielded the following results: m/z calcd.: 600.6, found: 602.3[M+2H+] and 642.2[M+2H++K+] (FIG. 8B).

Example 5: Self-Assembled Nanoparticles of the Drug Conjugates

The drug conjugates FRRG-DOX (SEQ ID NO: 7), GGGGFRRG-DOX (SEQ ID NO: 8), GGFRRGGG-DOX (SEQ ID NO: 9), and FRRGGGGG-DOX (SEQ ID NO: 10) synthesized in Examples 1-4 are conjugates in which the hydrophobic drug is conjugated to the amphiphilic peptide consisting of hydrophobic amino acids and hydrophilic amino acids and specifically degraded by cathepsin B. The drug conjugates spontaneously form spherical nanoparticles in solvents. Specifically, the spherical nanoparticles are formed by the drug conjugate molecules connected to each other. The spherical nanoparticles have a structure in which the hydrophobic moieties of the drug conjugate form a core and the hydrophilic moieties of the drug conjugate are exposed to the outside of the core.

The drug conjugate of Example 1, which was confirmed to be most effective among the drug conjugates of Examples 1-4, was dissolved in various solvents to characterize the self-assembled nanoparticles thereof.

Figure 1B:
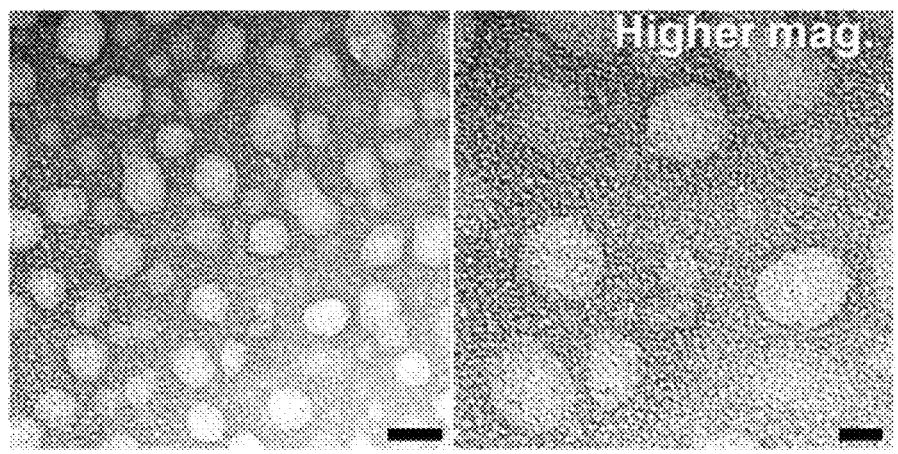
FIG. 1B shows TEM images of nanoparticles formed by self-assembly of the drug conjugate FRRG-DOX (SEQ ID NO: 7) in PBS solution containing saline (NaCl 0.9%)

FIG. 1B shows TEM images of nanoparticles formed by self-assembly of the drug conjugate FRRG-DOX (SEQ ID NO: 7) in PBS solution containing saline (NaCl 0.9%). The TEM images were measured using CM-200 (Philips, CA, USA).

As shown in FIG. 1B, the drug conjugate FRRG-DOX (SEQ ID NO: 7) of Example 1 in which the amphiphilic peptide was conjugated with the hydrophobic drug doxorubicin was found to form self-assembled nanoparticles when dissolved in physiological saline.

Figure 1C:
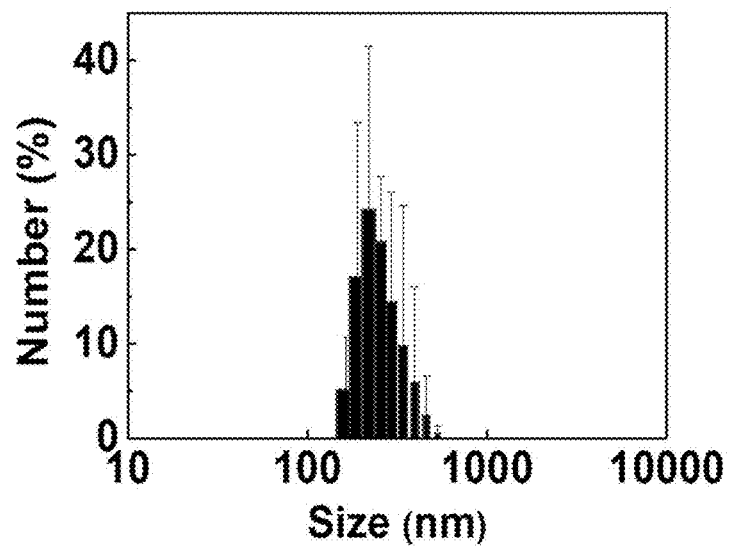
FIG. 1C shows the size distribution of the nanoparticles formed by self-assembly of the drug conjugate FRRG-DOX (SEQ ID NO: 7) in PBS solution containing saline (NaCl 0.9%), which was measured by dynamic light scattering.

FIG. 1C shows the size distribution of the nanoparticles formed by self-assembly of the drug conjugate FRRG-DOX (SEQ ID NO: 7) in PBS solution containing saline (NaCl 0.9%), which was measured by dynamic light scattering. The size distribution was measured using Zetasizer Nano ZS (Malvern Instruments, Worcestershire, U.K).

As shown in FIG. 1C, the self-assembled nanoparticles of Example 1 were found to have an average diameter of 100-1000 nm, preferably 50-500 nm.

Figure 1D:
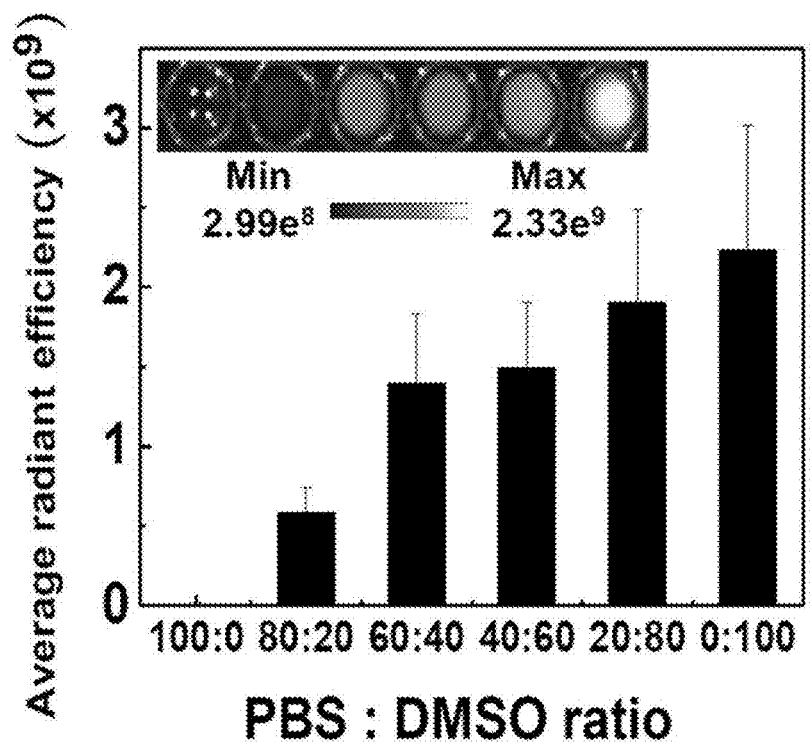
FIG. 1D shows images (top) and a histogram showing the fluorescence of self-assembled nanoparticles of a drug conjugate (FRRG-DOX) (SEQ ID NO: 7) of Example 1 in co-solvents of PBS and DMSO in different ratios, which were measured to observe whether the self-assembled nanoparticles were formed when the drug conjugate FRRG-DOX (SEQ ID NO: 7) was added.

FIG. 1D shows images (top) and a histogram showing the fluorescence of the self-assembled nanoparticles of the drug conjugate FRRG-DOX (SEQ ID NO: 7) of Example 1 in co-solvents of PBS and DMSO in different ratios, which were measured to observe whether the self-assembled nanoparticles were formed when the drug conjugate FRRG-DOX (SEQ ID NO: 7) was added.

As shown in FIG. 1D, the self-assembled nanoparticles were formed by the drug conjugate FRRG-DOX (SEQ ID NO: 7) of Example 1 in the buffers without using any drug carrier and their structure collapsed when an excess of DMSO was used.

Comparative Example 1: Synthesis of Drug Conjugate RRG-DOX (SEQ ID NO: 11)

A drug conjugate RRG-DOX (SEQ ID NO: 11) was prepared in the same manner as in Example 1, except that a hydrophilic peptide having the sequence RRG set forth in SEQ ID NO: 5 synthesized in accordance with a solid state peptide synthesis protocol was used instead of the hydrophilic peptide having the sequence FRRG set forth in SEQ ID NO: 1.

Experimental Example 1: Analysis of In Vitro Specificity of FRRG-DOX (SEQ ID NO: 7) Prepared in Example 1 for Cathepsin B In this example, the specificity of FRRG-DOX (SEQ ID NO: 7) prepared in Example 1 for cleavage by cathepsin B was investigated. First, cathepsin B (10 µg/ml) was dissolved in 25 mM 2-(N-morpholine)-ethanesulphonic acid (MES) buffer. The drug conjugate FRRG-DOX (SEQ ID NO: 7) (100 µM) of Example 1 was added to the cathepsin B solution. The divided portions of the mixture were incubated at 37 □ for 0, 1, 3, 6, and 9 h. The drug conjugate of Example 1 having reacted with cathepsin B was analyzed by reverse-phase HPLC (Agilent Technologies 1200 series, Agilent Technologies, USA) using a C18 analytical column (10:90 H$_2$O:acetonitrile to 60:40 H$_2$O:acetonitrile) for 20 min at 210 nm.

The drug conjugate of Example 1 was allowed to react with other enzymes (10 µg/ml cathepsins D, E, and L) and PBS buffer only (in this case, a non-enzymatic hydrolysis product was obtained) and the reaction products were analyzed by HPLC at 37° C. for 9 h.

Figure 1E:
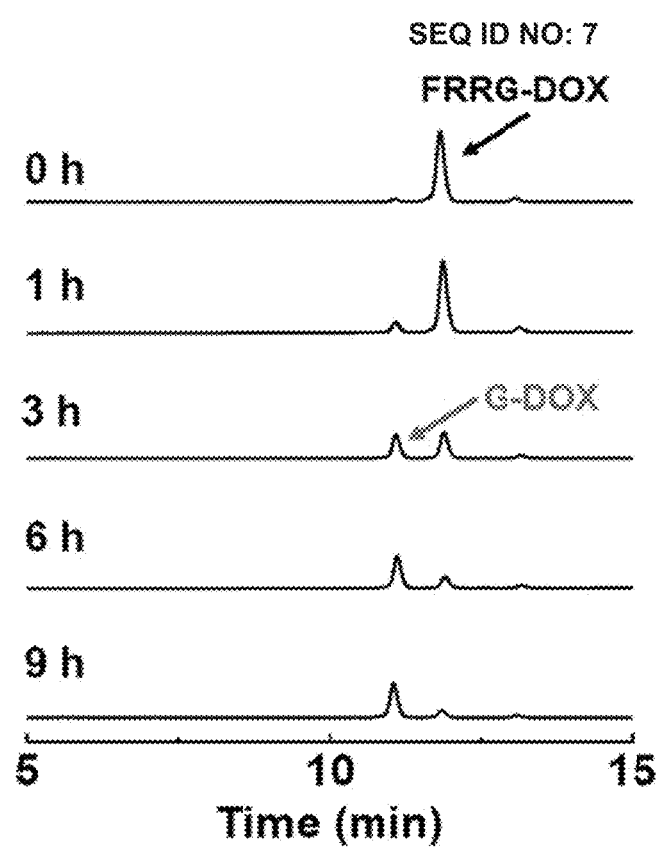
FIG. 1E shows the HPLC results of the drug conjugate FRRG-DOX (SEQ ID NO: 7) of Example 1 during incubation with cathepsin B for 9 h.

FIG. 1E shows the HPLC results of the drug conjugate FRRG-DOX (SEQ ID NO: 7) prepared in Example 1 during incubation with cathepsin B for 9 h.

As shown in FIG. 1E, the drug conjugate FRRG-DOX (SEQ ID NO: 7) of Example 1 was successfully cleaved by cathepsin B upon reaction with cathepsin B and the resulting cleaved peptide was G-DOX liberated from FRRG-DOX (SEQ ID NO: 7). The cleavage product was identified by MALDI-TOF MS.

Figure 1F:
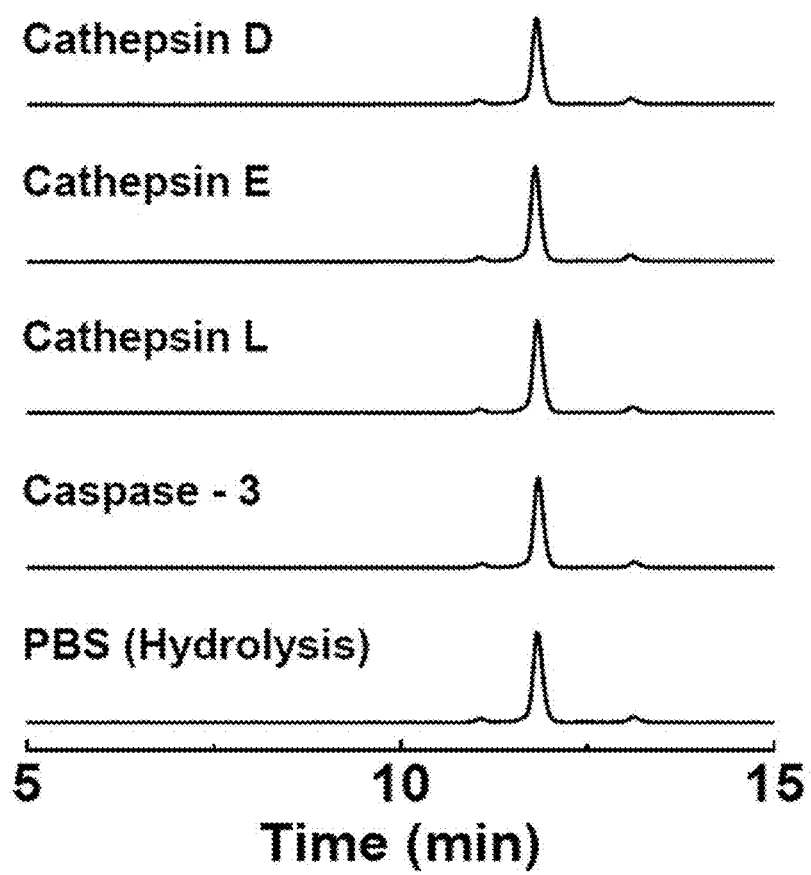
FIG. 1F shows the HPLC results of the drug conjugate FRRG-DOX (SEQ ID NO: 7) of Example 1 during incubation with other enzymes, including cathepsin D, cathepsin E, cathepsin L, and caspase-3.

FIG. 1F shows the HPLC results of the drug conjugate FRRG-DOX (SEQ ID NO: 7) during incubation with other enzymes, including cathepsin D, cathepsin E, cathepsin L, and caspase-3.

As shown in FIG. 1F, the drug conjugate FRRG-DOX (SEQ ID NO: 7) of Example 1 was not degraded by cathepsin D, cathepsin E, cathepsin L, and caspase-3 except cathepsin B. That is, the drug conjugate FRRG-DOX (SEQ ID NO: 7) was specifically cleaved by cathepsin B. The drug conjugate FRRG-DOX (SEQ ID NO: 7) of Example 1 was non-enzymatically hydrolyzed in phosphate buffered saline (PBS) but was found to be very stable in phosphate buffered saline.

Experimental Example 2: In Vitro Intracellular Delivery of the Drug Conjugate of Example 1

In this example, intracellular uptakes of doxorubicin (Free DOX) and FRRG-DOX (SEQ ID NO: 7) of Example 1 were observed. First, HT-29 human colorectal cancer cells were plated on 35 mm cover glass bottom dishes ($1\times10^5$ cells each), treated with doxorubicin (Free Dox, 10 μM) and FRRG-DOX (SEQ ID NO: 7) (10 μM) of Example 1, and cultured in a carbon dioxide incubator at 37 □ for 48 h.

The same procedure was repeated except that cell lines U87, A549, MCF7, MDA-MB231, H9C2, HDF, and Hela were used instead of HT29 cells. Cells were treated with a cell fixative and nuclei were stained by treatment with a solution of 4,6-diamidino-2-phenylindole (DAPI) for 10 min. The absorbed doxorubicin and 4,6-diamidino-2-phenylindole were observed by confocal microscopy.

The expression of doxorubicin in HT29 cells was investigated. To this end, the culture solution was treated with DBCO-Cy5 (5 μM each) and cultured in an incubator at 37° C. for different periods of time. Cells were washed with Dulbecco's phosphate buffered saline (DPBS) to remove unreacted DBCO-Cy5. Cells were treated with a cell fixative for 15 min and nuclei were stained by treatment with a solution of 4,6-diamidino-2-phenylindole (DAPI) for 10 min. The fluorescence of DBCO-Cy5 bound with the expressed doxorubicin was observed by confocal microscopy.

Figure 2A:
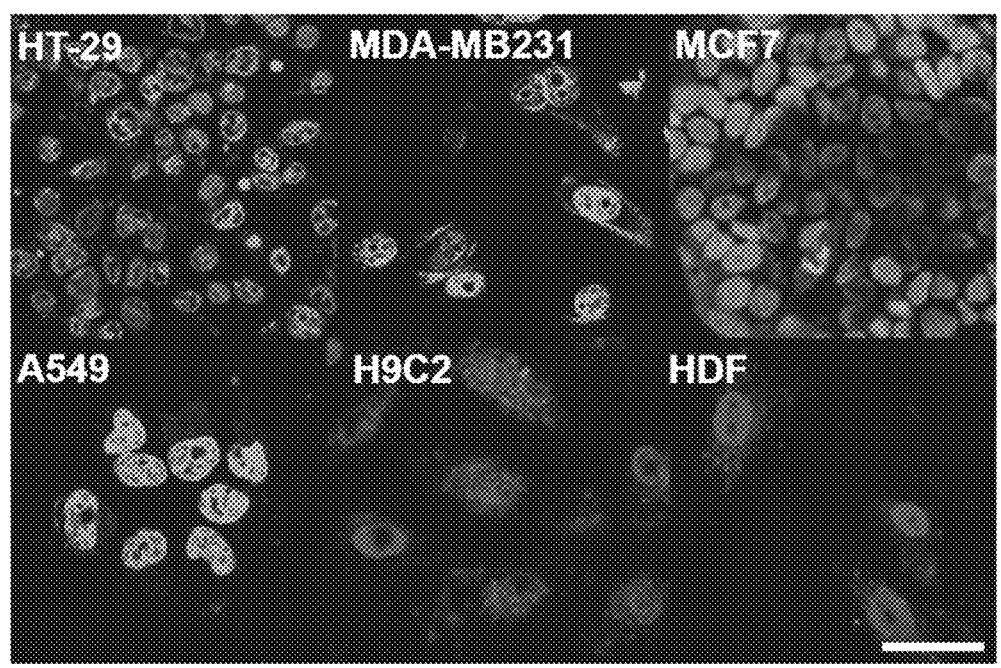
FIG. 2A shows confocal microscopy images of tumor cells (HT29 human colon cancer cells, MDA-MB231 human breast cancer cells, MCF7 human breast cancer cells, A549 human lung cancer cells, and U87 brain cancer cells) and normal cells (H9C2 Rattus cardiac cells and human dermal fibroblasts (HDF)) treated with a drug conjugate (FRRG-DOX) (SEQ ID NO: 7) of Example 1.

FIG. 2A shows confocal microscopy images of tumor cells (HT29 human colon cancer cells, MDA-MB231 human breast cancer cells, MCF7 human breast cancer cells, A549 human lung cancer cells, and U87 brain cancer cells) and normal cells (H9C2 Rattus cardiac cells and human dermal fibroblasts (HDF)) treated with the drug conjugate FRRG-DOX (SEQ ID NO: 7) of Example 1 (bar=50 μm).

Figure 2B:
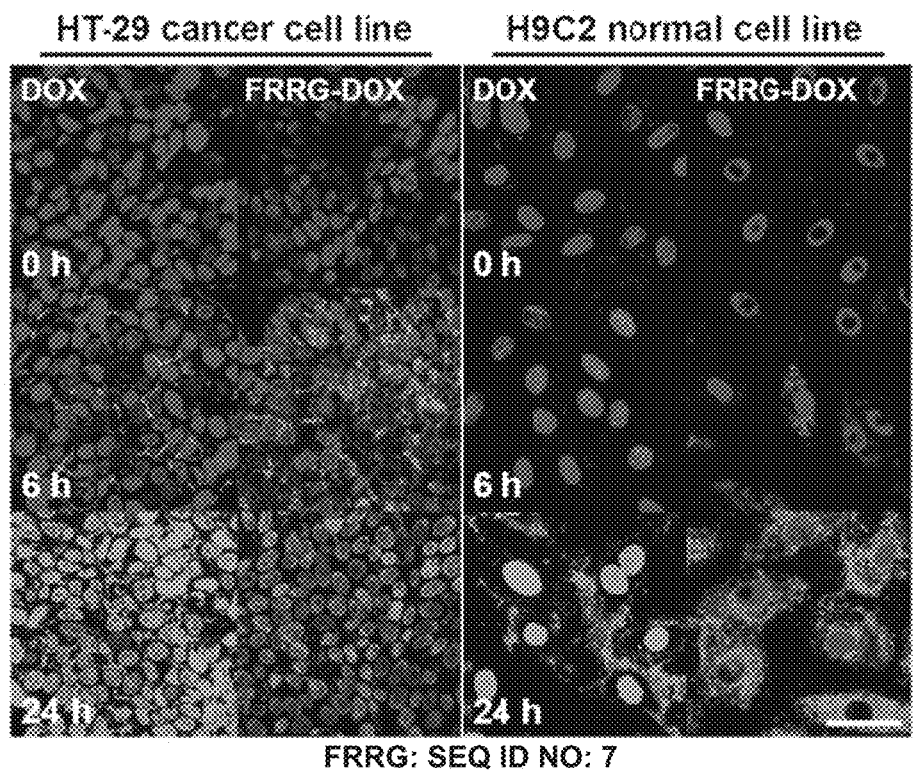
FIG. 2B shows confocal microscopy images of tumor cells (HT29) and normal cells (H9C2) obtained at different time points after treatment with the drug conjugate FRRG-DOX (SEQ ID NO: 7) of Example 1 and treatment with doxorubicin alone (Free DOX)

FIG. 2B shows confocal microscopy images of tumor cells (HT29) and normal cells (H9C2) obtained at different time points after treatment with the drug conjugate FRRG-DOX (SEQ ID NO: 7) of Example 1 and treatment with doxorubicin alone (Free DOX) (bar=50 μm).

Figure 2C:
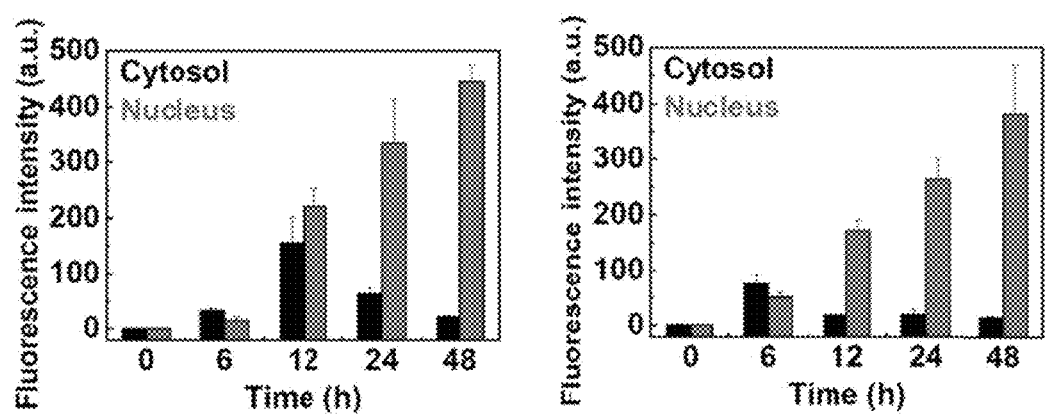
FIGS. 2C and 2D show quantitative results of FIG. 2B, specifically for tumor cells (HT29) and normal cells (H9C2) treated with the drug conjugate FRRG-DOX (SEQ ID NO: 7) of Example 1, respectively.
Figure 2D:
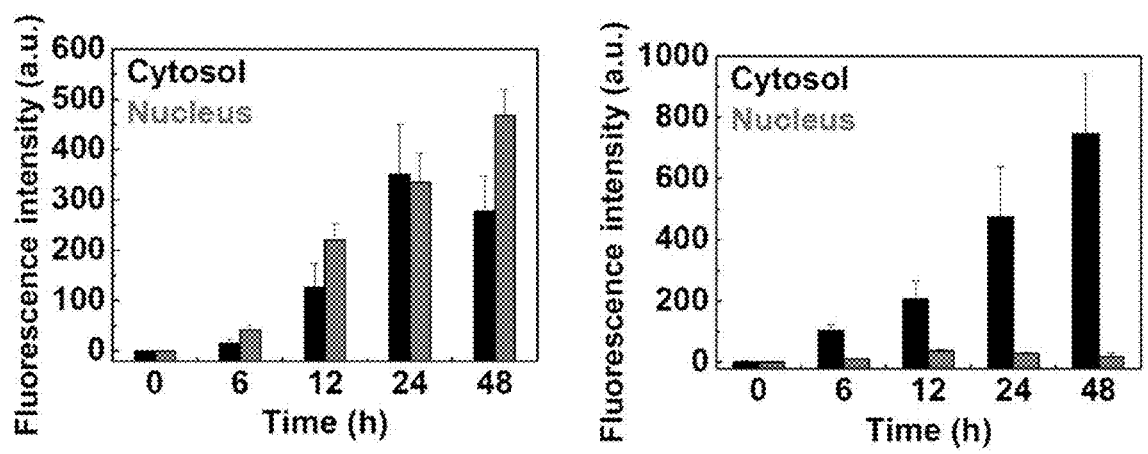

FIGS. 2C and 2D show quantitative results of FIG. 2B, specifically for tumor cells (HT29) and normal cells (H9C2) treated with the drug conjugate FRRG-DOX (SEQ ID NO: 7) of Example 1, respectively.

As shown in FIG. 2A, functional differences of FRRG-DOX (SEQ ID NO: 7) (Example 1) in tumor cells and normal cells were investigated in order to confirm whether FRRG-DOX (SEQ ID NO: 7) was specifically degraded by cathepsin B and showed drug toxicity.

As shown in FIGS. 2B, 2C, and 2D, the uptakes of FRRG-DOX (SEQ ID NO: 7) in cells and nuclei were observed over time. As a result, the uptakes of FRRG-DOX (SEQ ID NO: 7) in HT29 tumor cells and H9C2 normal cells were significantly different.

In vitro cell viabilities were analyzed by evaluating the cytotoxicities of doxorubicin (Free DOX) and FRRG-DOX (SEQ ID NO: 7) of Example 1. First, HT-29 cells were plated in a 96-well plate at a density of $1\times10^4$ cells/well. After stabilization, HT-29 cells were treated with various concentrations (0.01, 0.1, 1, 10, 100 and 200 μM) of doxorubicin (Free DOX) and FRRG-DOX (SEQ ID NO: 7) of Example 1 and cultured at 37° C. for 48 h. Then, 10 μg of CCK solution was added to each well. After further culture for 30 min, the absorbance of each 96-well plate at 450 nm was analyzed using a microplate reader (VERSA-max™, Molecular Devices Corp., Sunnyvale, Calif.). For comparison, the cell viabilities (%) of H9C2 cells (normal cells) were measured in the same manner as described above.

Figure 2E:
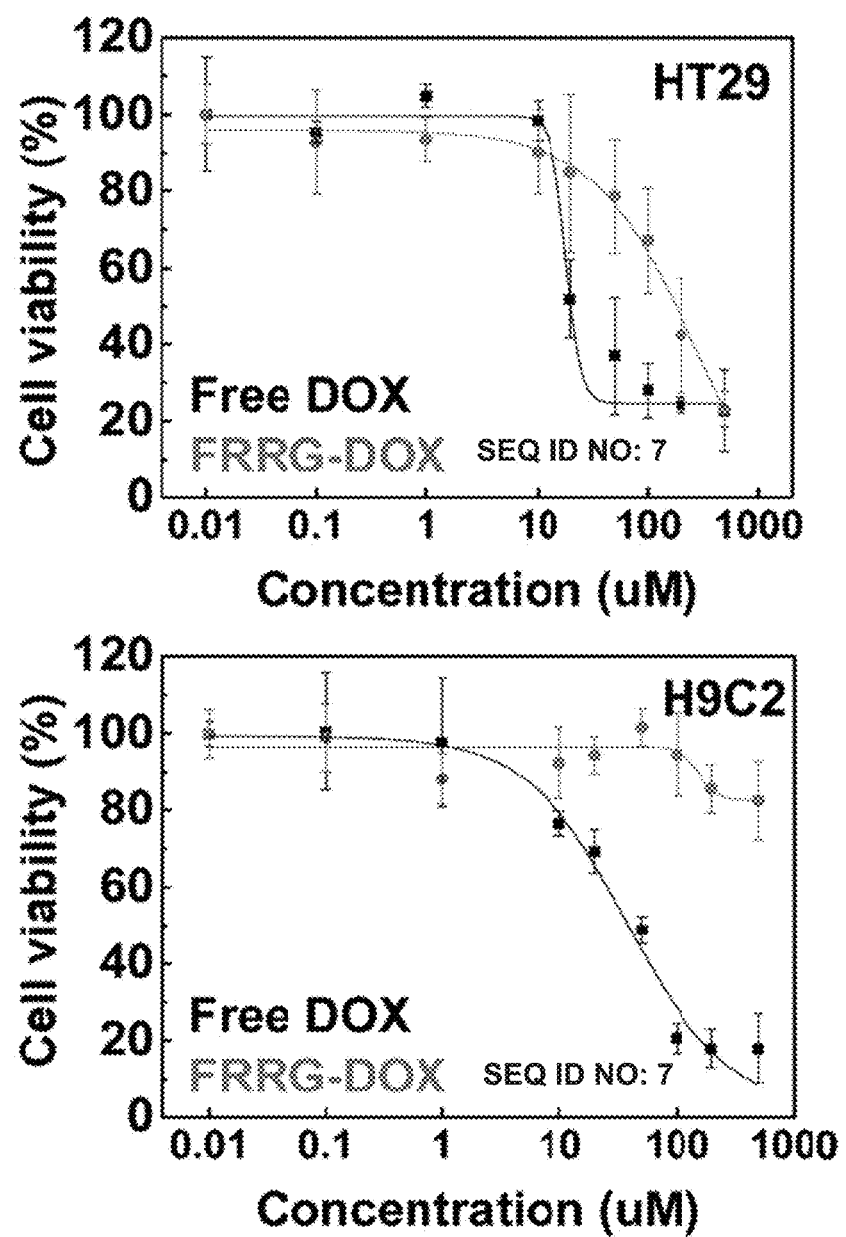
FIG. 2E shows cell viabilities (%) of tumor cells (HT29, top) and normal cells (H92C, bottom) treated with various concentrations (0.01-500 µM) of doxorubicin (Free DOX) and the drug conjugate FRRG-DOX (SEQ ID NO: 7) of Example 1.

FIG. 2E shows cell viabilities (%) of tumor cells (HT29, top) and normal cells (H92C, bottom) treated with various concentrations (0.01-500 μM) of doxorubicin (Free DOX) and the drug conjugate FRRG-DOX (SEQ ID NO: 7) of Example 1.

The therapeutic effect of FRRG (SEQ ID NO: 1) on tumor cells was confirmed by comparing with that on normal cardiomyocytes. Specifically, FRRG-DOX (SEQ ID NO: 7) of Example 1 showed no toxicity to normal cells and selectively inhibited the growth of tumor cells, as shown in FIG. 2E.

In tumor cells, there was no substantial difference in cell viability between the group treated with FRRG-DOX (SEQ ID NO: 7) of Example 1 and the group treated with doxorubicin alone (Free-DOX). In normal cells, there was a significant difference in cell viability between the group treated with FRRG-DOX (SEQ ID NO: 7) of Example 1 and the group treated with doxorubicin alone (Free DOX).

That is, FRRG-DOX (SEQ ID NO: 7) was successfully cleaved by cathepsin B in tumor cells, and as a result, the activated drug was not found in the normal cell nuclei but was found mainly in the tumor cell nuclei.

When treated with FRRG-DOX (SEQ ID NO: 7), doxorubicin was not accumulated in the normal cell nuclei but was accumulated in the tumor cell nuclei. It was found that doxorubicin accumulated in tumor cell nuclei stops the replication of the tumor cells to inhibit the growth of the tumor cells or kill the tumor cells.

These results conclude that FRRG-DOX (SEQ ID NO: 7) has an in vitro prophylactic or therapeutic effect against tumor cells.

The concentration of cathepsin B was investigated by the following procedure. First, HT-29, A549, MCF7, MDA-MB231, H9C2, and HDF cells ($1\times10^6$ each) were plated and cultured in 100 mm cell culture dishes. After stabilization, cells were washed three times with DPBS and dispersed in lysis buffer (1% sodium deoxycholate, 0.1% SDS, 1% NP-40, 25 mM tris-HCl, 150 mM NaCl, and 1% protease inhibitor). The collected lysates were spun down at 12,000 rpm for 10 min at 4° C. to remove cell debris and protein concentrations in the lysates were quantified using a BCA analysis kit. The quantified proteins of each sample were mixed with 1×sodium dodecyl sulfate (SDS) as a loading buffer and heated for 5 min. Thereafter, 10 μg of the proteins were separated on a 12% SDS-polyacrylamide gel. Then, the separated proteins were transferred to NC membranes and treated in blocking solution (TBST buffer supplemented with 5% bovine serum albumin (10 mol/L Tris, pH 7.4, 100 mol/L NaCl and 0.1% Tween 20)) at 25° C. for 1 h. Then, the membranes were incubated in blocking solution supplemented with mouse anti-human cathepsin B antibody at 4° C. overnight, washed five times with TBST buffer, and treated with blocking solution supplemented with 0.2 μg/ml of rabbit anti-goat IgG-HRP antibody. Washing was repeated five times. Thereafter, pro-cathepsin B (37 KDa) and cathepsin B (25 KDa) bands were detected using an ECL system. The HRP signal intensities of cathepsin B in cells were measured and analyzed using the Image J software.

Figure 2F:
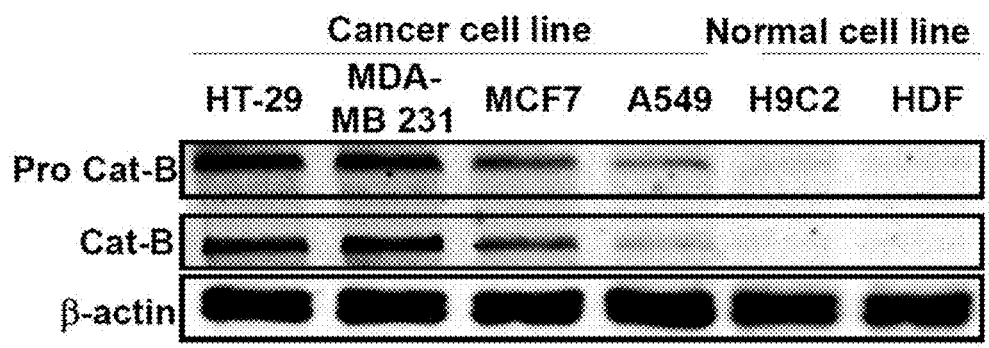
FIG. 2F shows overexpression levels of cathepsin B in various cancer cells, which were determined by Western blotting.
Figure 2G:
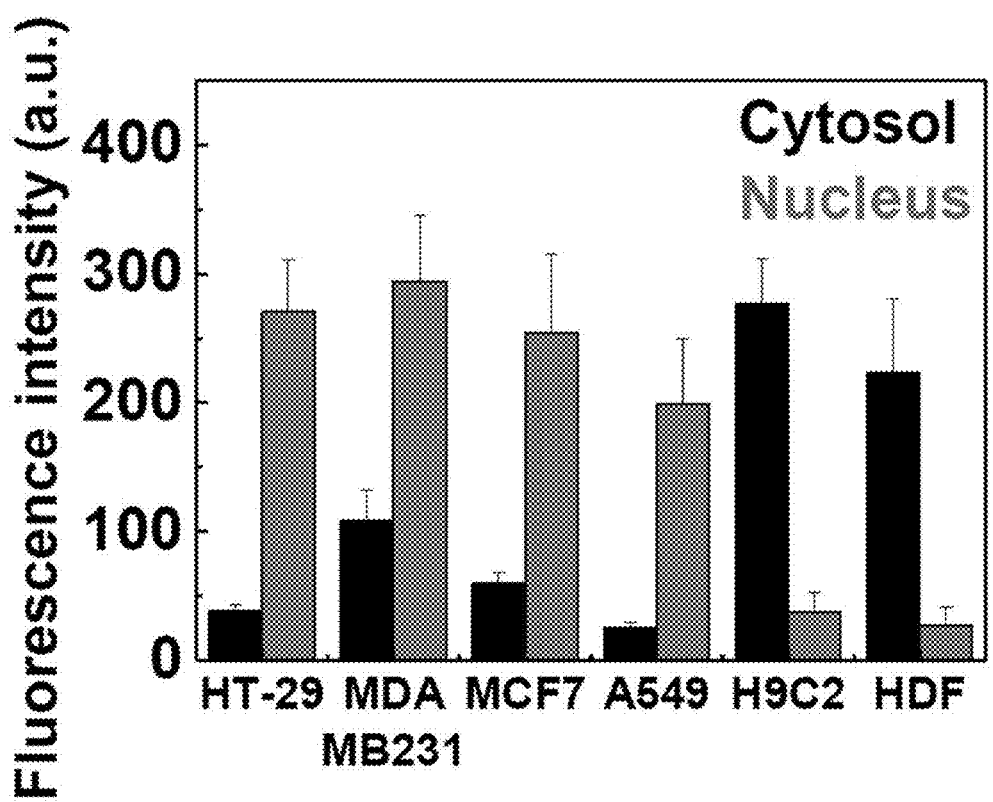
FIG. 2G quantifies the Western blotting results of FIG. 2F using the Image J program.

FIG. 2F shows overexpression levels of cathepsin B in various cancer cells, which were determined by Western blotting, and FIG. 2G quantifies the Western blotting results of FIG. 2F using the Image J program.

As shown in FIGS. 2F and 2G, cathepsin B was overexpressed in tumor cells, including HT29 (human colon adenocarcinoma), MDA-MB231 (human breast adenocarcinoma), and MDA-MB231 (human breast adenocarcinoma) cells, unlike in normal cells.

The expression level of cathepsin B in A549 (human lung cancer) was low but was significantly high compared to those of other enzymes (not shown). In contrast, no substantial expression of cathepsin B was observed in normal cells.

These results collectively suggest that the drug of FRRG-DOX (SEQ ID NO: 7) is absorbed into cells based on the activity of cathepsin B expressed only in tumor cells. When treated with FRRG-DOX (SEQ ID NO: 7), doxorubicin was accumulated in tumor cells, including HT-29, MDA-MB231, MCF7, and A549 cells, but was not accumulated in normal cells, including H9C2 and HDF cells.

The most serious problem of general therapeutic agents for cancer is their toxicity in normal cells as well as in tumor cells. Particularly, the most serious side effect of doxorubicin is toxicity to cardiac cells. FRRG-DOX (SEQ ID NO: 7) showed no activity on H9C2 cells, neonatal myocardial cells, and doxorubicin was not accumulated in nuclei.

These results conclude that FRRG-DOX (SEQ ID NO: 7) is appropriately designed to very specifically respond to tumor cells and has the function of clearly distinguishing tumor cells and normal cells. In addition, the drug conjugate FRRG-DOX (SEQ ID NO: 7) can solve the problems of conventional therapeutic agents for cancer and has the potential to offer a novel therapeutic agent for cancer with markedly improved stability and specificity.

Experimental Example 3: Evaluation of Expression Efficiency of Doxorubicin of FRRG-DOX (SEQ ID NO: 7) in Cancer Cells Using Cathepsin B Inhibitor In this example, the specificity of FRRG-DOX (SEQ ID NO: 7) of Example 1 for cathepsin B was investigated. To this end, cathepsin B siRNA (150 nM) containing lipofectamine 2000 was allowed to react at 37° C. for 30 min to prepare a lipofectamine-siRNA conjugate.

$1 \times 10^5$ HT-29 human-derived colorectal cancer cells were plated on a 35 mm cover glass bottom dish, cultured for 24 h, treated with the lipofectamine-siRNA conjugate (50 μg/L), cultured for 4 h, treated with FRRG-DOX (SEQ ID NO: 7) (5 μM) of Example 1, and cultured in a carbon dioxide incubator at 37° C. for 24 h.

The treated HT-29 cells were washed twice with DPBS, fixed in 10% formaldehyde for 20 min in the dark, washed with DPBS, and stained with Hoechest (No. 33258) at room temperature for 10 min. Cells were observed under a confocal laser microscope (Leica TCS SP8, Leica Microsystems GmbH) using 405 diode (405 nm), Ar (458, 488, and 514 nm) and He—Ne (633 nm) lasers. The NIRF signal intensities of the drug conjugate and doxorubicin in cells were analyzed using the Image J software (National Institutes of Health (NIH), Bethesda, USA).

Figure 2H:
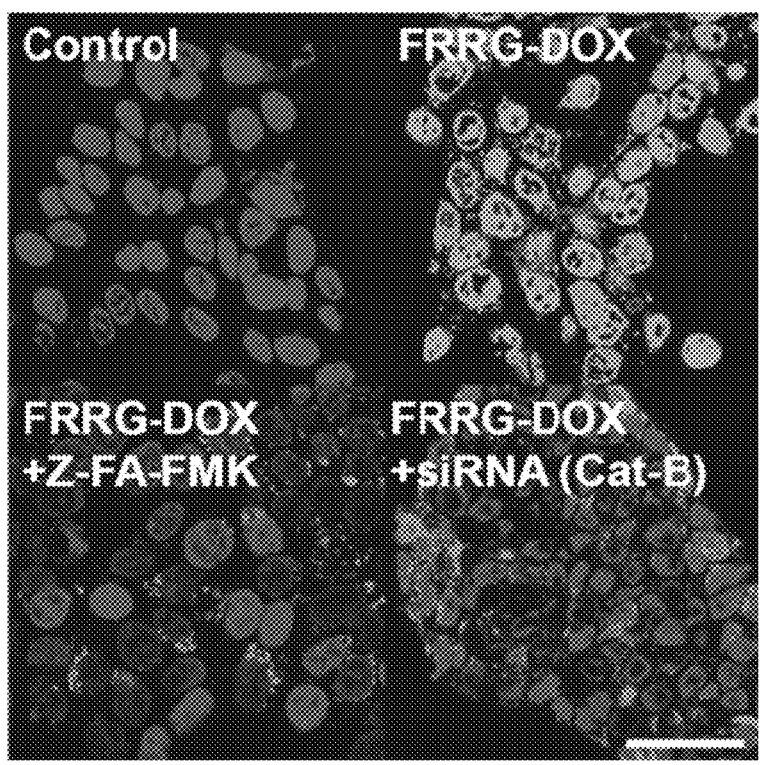
FIG. 2H shows confocal microscopy images of HT29 cells sequentially treated with a lipofectamine-siRNA conjugate having an inhibitory effect on cathepsin B and the drug conjugate (FRRG-DOX) (SEQ ID NO: 7) ("FRRG-DOX+siRNA(Cat-B)"). Here, the red colors indicate doxorubicin and the blue colors indicate cell nuclei stained with DAPI. "FRRG-DOX" (SEQ ID NO: 7) shows HT29 cells untreated with the lipofectamine-siRNA conjugate but treated with FRRG-DOX (SEQ ID NO: 7) alone.

FIG. 2H shows confocal microscopy images of HT29 cells treated with FRRG-DOX (SEQ ID NO: 7) under different conditions.

In FIG. 2H, "FRRG-DOX (SEQ ID NO: 7)" indicates the treatment of HT29 cells with FRRG-DOX (SEQ ID NO: 7) without treatment with the lipofectamine-siRNA conjugate, "FRRG-DOX+Z-FA-FMK" indicates the treatment of HT29 cells with Z-FA-FMK (cathepsin activity inhibitor) and subsequent FRRG-DOX (SEQ ID NO: 7), and "FRRG-DOX+siRNA(Cat-B)" indicates the treatment of HT-29 cells with the lipofectamine-siRNA conjugate having an inhibitory effect on cathepsin B and subsequent FRRG-DOX (SEQ ID NO: 7). The red colors indicate doxorubicin and the blue colors indicate cell nuclei stained with DAPI.

Figure 2I:
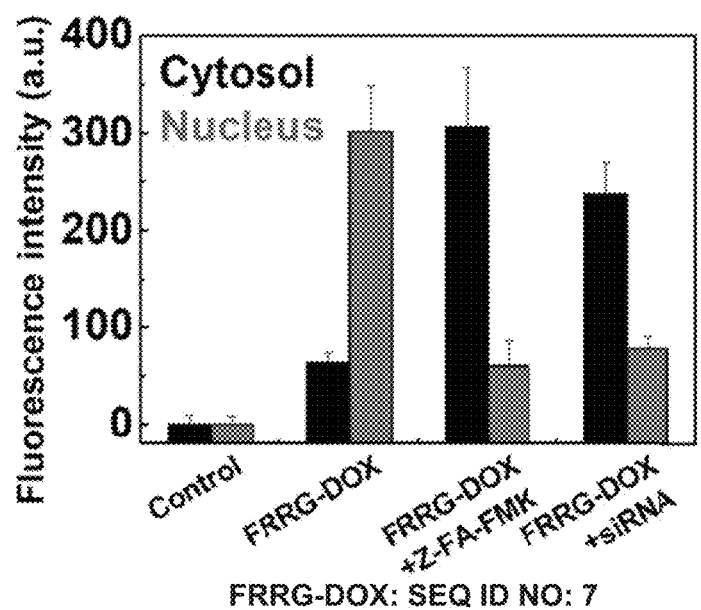
FIG. 2I quantifies the results of fluorescence intensities determined from FIG. 2H.

FIG. 2I quantifies the results of fluorescence intensities determined from FIG. 2H.

As shown in FIGS. 2H and 2I, when HT-29 cells were treated with the conjugate of small interfering RNA(siRNA) having an inhibitory effect on cathepsin B and lipofectamine 2000, followed by treatment with the drug conjugate, the amount of doxorubicin absorbed into the cell nuclei was reduced. Particularly, the difference was made clear when the quantitative values of doxorubicin absorbed into and accumulated in the cells were compared.

These results demonstrate the specific activity of the drug conjugate FRRG-DOX (SEQ ID NO: 7) on cathepsin B. In conclusion, the drug conjugate FRRG-DOX (SEQ ID NO: 7) is specifically cleaved by cathepsin B expressed in tumor cells to deliver and release the drug into cells.

Experimental Example 4: Evaluation of Expression Efficiency of Doxorubicin of FRRG-DOX (SEQ ID NO: 7) Via Direct Injection into Tissues of Tumor Animal Models Animal experiments were performed in compliance with the guidelines of the Korea Institute of Science and Technology (KIST) and were approved by the Institutional Committees.

5.5-week-old male athymic nude mice (20-25 g) were purchased from Nara Bio INC (Gyeonggi-do, Korea). $1 \times 10^7$ HT-29 cells were inoculated into both thighs of each male nude mouse (n=6) to construct a tumor animal model. 5 weeks after inoculation, the tumor size reached 250-300 mm$^3$.

First, the activity of cathepsin B in tumor tissues was investigated. When the tumor size of the tumor animal model reached 250-300 mm$^3$, cathepsin B siRNA having an inhibitory effect on cathepsin B was directly injected into the tumor tissues. After 1 day, FRRG-DOX (SEQ ID NO: 7) of Example 1 was injected into both tumor tissues twice a day (4 mg/kg each). After another 1 day, 100 μg of azadibenzocyclooctyne-Cy5.5 (DBCO-Cy5.5) (200 μL) was administered intravenously to target doxorubicin expressed in tumor tissues. 6 h after administration, near-infrared fluorescence images were recorded. Organs were excised and fluorescence remaining therein was measured. NIRF intensity in tumor ROIs was quantified using the Living Image software (PerkinElmer, USA).

Frozen sections of the tumor tissues were constructed and fluorescence remaining therein was observed under a confocal microscope. The analysis procedure was performed in the same manner as mentioned in Experimental Examples 1, 2, and 3.

Figure 3A:
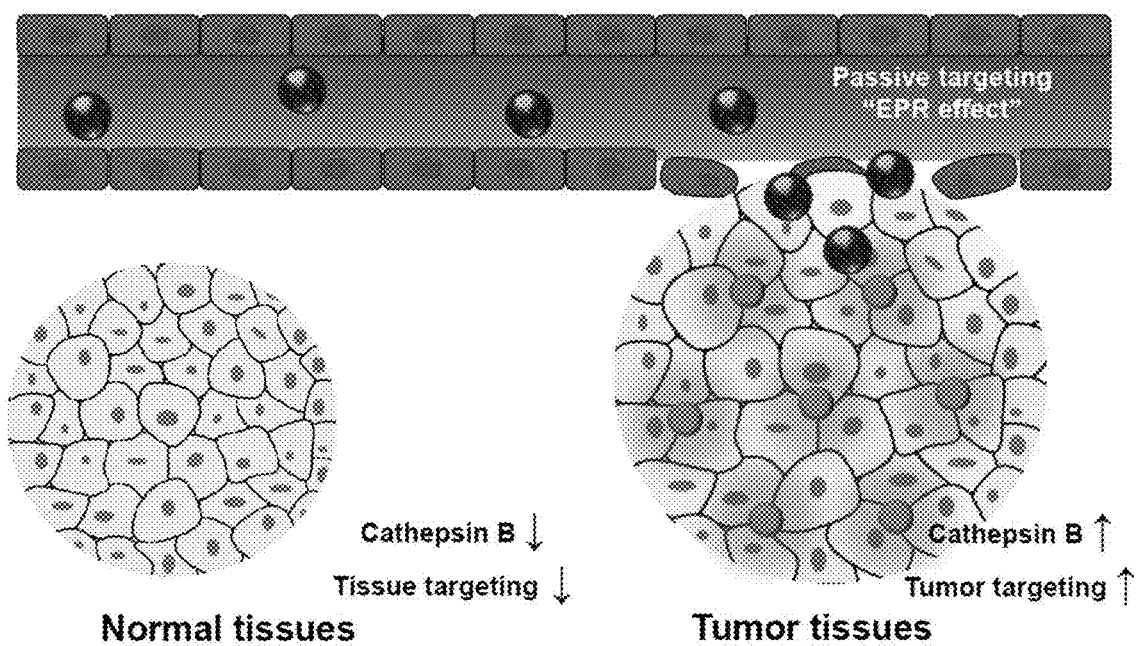
FIG. 3A schematically shows the in vivo mechanism of action of a drug conjugate (FRRG-DOX) (SEQ ID NO: 7) according to the present invention.

FIG. 3A schematically shows the in vivo mechanism of action of the drug conjugate FRRG-DOX (SEQ ID NO: 7). The nanoparticles based on FRRG-DOX (SEQ ID NO: 7) (Example 1) could be accumulated in tumor tissues by the EPR effect. This is because the amphiphilic peptide contributes to the formation of the nanoparticles due to the presence of phenylalanine and arginine. In addition, the self-assembled nanoparticles spontaneously formed by the drug conjugate FRRG-DOX (SEQ ID NO: 7) maintained their flexibility and stability even without using a linker. Therefore, the self-assembled nanoparticles are very useful as drug carriers and prodrugs.

Figure 3B:
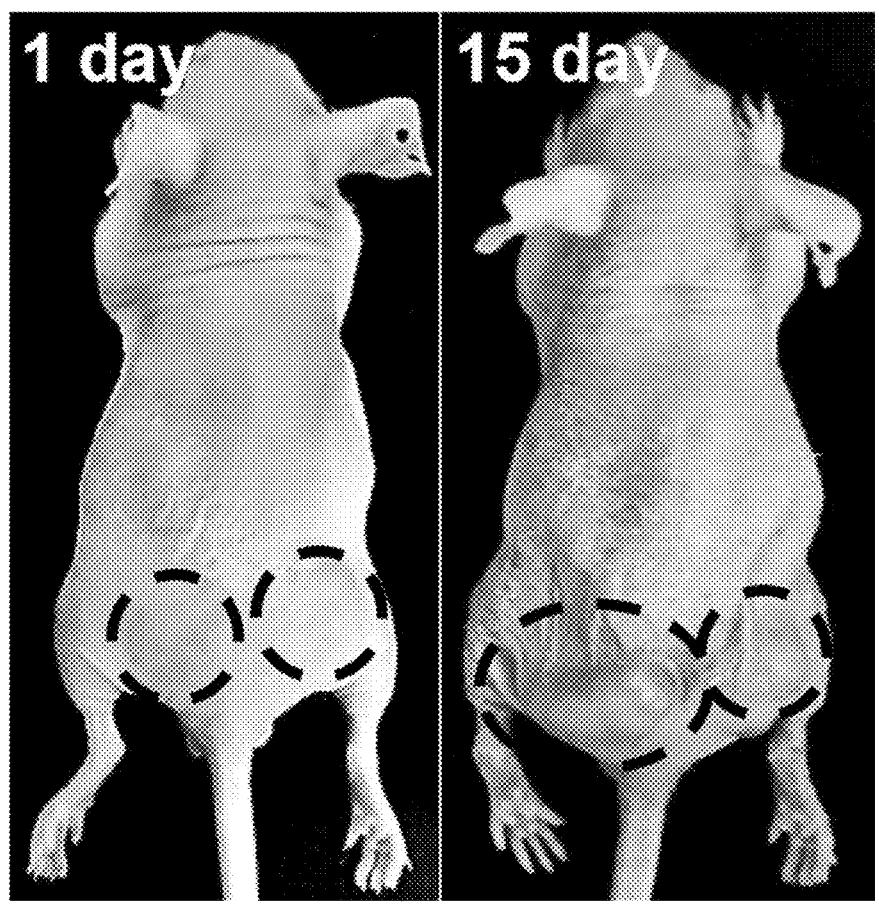
FIG. 3B shows photographs of a tumor animal model taken on days 1 and 15 after inoculation of HT29 tumor into the right and left flanks of the tumor animal model and administration of a cathepsin B siRNA inhibitor to the left tumor only, which were obtained to observe a change in the condition of the animal model and evaluate the cytotoxicity of the cathepsin B siRNA inhibitor in the animal model.
Figure 3C:
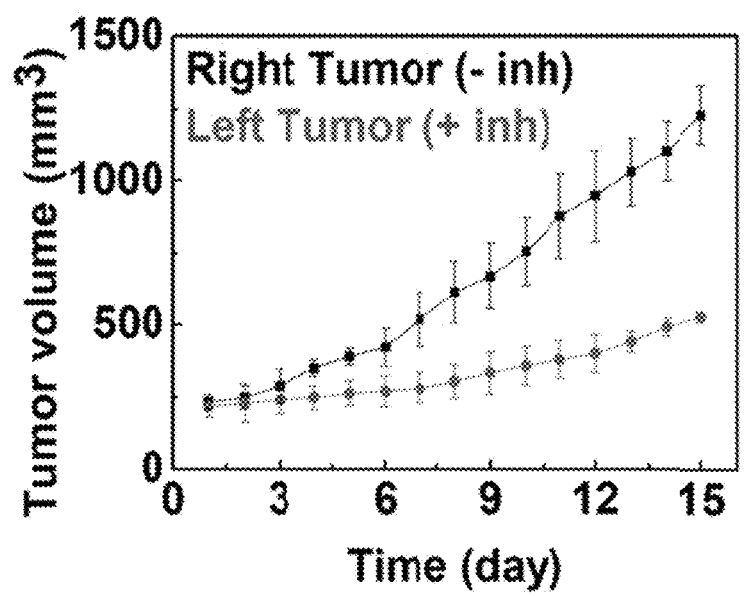
FIG. 3C shows sizes of tumor tissues excised from the animal tumor model of FIG. 3B at different time points.

FIG. 3B shows photographs of a tumor animal model taken on days 1 and 15 after inoculation of HT29 tumor into the right and left flanks of the tumor animal model and administration of a cathepsin B siRNA inhibitor to the left tumor only, which were obtained to observe a change in the condition of the animal model and evaluate the cytotoxicity of the cathepsin B siRNA inhibitor in the animal model. FIG. 3C shows sizes of tumor tissues excised from the animal tumor model of FIG. 3B at different time points.

As shown in FIGS. 3B and 3C, when the cathepsin B inhibitor was administered with FRRG-DOX (SEQ ID NO: 7) of Example 1, no anticancer effect was observed visually. In contrast, when tumor tissues untreated with the cathepsin B inhibitor were treated with FRRG-DOX (SEQ ID NO: 7) of Example 1, the size of the tumor tissues was found to be similar to that of normal tissues. These results demonstrate the presence of a large quantity of cathepsin B in tumor tissues, like in tumor cells, and the non-accumulation of doxorubicin in other normal tissues where cathepsin B is not substantially expressed.

Referring to FIG. 3C, the administration of cathepsin B inhibiting siRNA reduced the activation of FRRG-DOX (SEQ ID NO: 7) in tumor tissues, and as a result, the tumor size increased ~5-fold compared to the tumor size after FRRG-DOX (SEQ ID NO: 7) was administered but cathepsin B siRNA was not administered. From these results, it can be concluded that the drug conjugate FRRG-DOX (SEQ ID NO: 7) is activated only in the presence of cathepsin B.

Selective activation of FRRG-DOX (SEQ ID NO: 7) was investigated in more detail. To this end, the left tumor tissues were treated with cathepsin B inhibiting siRNA and the right tumor tissues were untreated with cathepsin B inhibiting siRNA. The average radiation values (fluorescence intensities) of the tumor tissues excised from both flanks were measured using a probe capable of cathepsin B detection. As a consequence, the activity of cathepsin B was maintained only in the right tumor tissues (not shown). These experimental results are an extension of the experiments of FIG. 3 and confirm that the target cathepsin B is expressed only in tumor tissues and the used cathepsin B siRNA effectively inhibits cathepsin B, making the experimental results using cathepsin B siRNA reliable.

Experimental Example 5: Evaluation of Expression Efficiency of Doxorubicin of FRRG-DOX (SEQ ID NO: 7) Via Intravenous Administration to Tumor Animal Models—1

In this example, the in vivo anticancer effects of doxorubicin (Free DOX) and FRRG-DOX (SEQ ID NO: 7) of Example 1 were investigated. First, 1×107 HT-29 cells were directly injected into the right flank of each tumor animal model constructed in 1) (n=4 per group). When the tumor size reached ~250-300 mm3, doxorubicin (Free DOX, 5 mg/kg) and FRRG DOX (SEQ ID NO: 7) of Example 1 (5 mg/kg) were administered intravenously once every three days for 15 days.

DPBS (200 µl each) was injected intravenously into tumor animal models once every three days for 15 days (control).

The therapeutic efficacies of Free DOX, FRRG-DOX (SEQ ID NO: 7), and the control were compared by measuring the tumor volumes (maximum diameter×minimum diameter 2×0.53) for 15 days. The viabilities and weights of the tumor animal models were measured once a day for 15 days. The accumulations of Free DOX and FRRG-DOX (SEQ ID NO: 7) in the tumor tissues of the tumor animal models were monitored using IVIS Lumina Series III (PerkinElmer, Massachusetts, USA). The fluorescence intensities of Free DOX and FRRG-DOX (SEQ ID NO: 7) in the tumor tissues were quantified using the Living Image software (PerkinElmer, Massachusetts, USA).

Figure 3D:
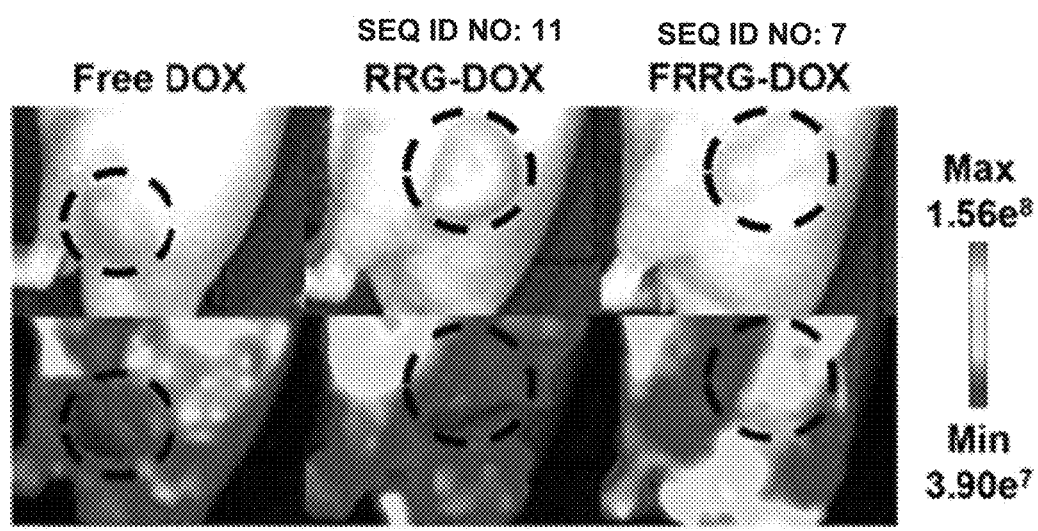
FIG. 3D shows doxorubicin-targeting near-infrared fluorescence images of tumor animal models administered doxorubicin alone (Free DOX), RRG-DOX (SEQ ID NO: of Comparative Example 1 (RRG-DOX) (SEQ ID NO: 11), and the drug conjugate FRRG-DOX (SEQ ID NO: 7) of Example 1.

FIG. 3D shows doxorubicin-targeting near-infrared fluorescence images of the tumor animal models administered doxorubicin alone (Free DOX), RRG-DOX (SEQ ID NO: 11) of Comparative Example 1 (RRG-DOX (SEQ ID NO: 11)), and the drug conjugate FRRG-DOX (SEQ ID NO: 7) of Example 1.

Figure 3E:
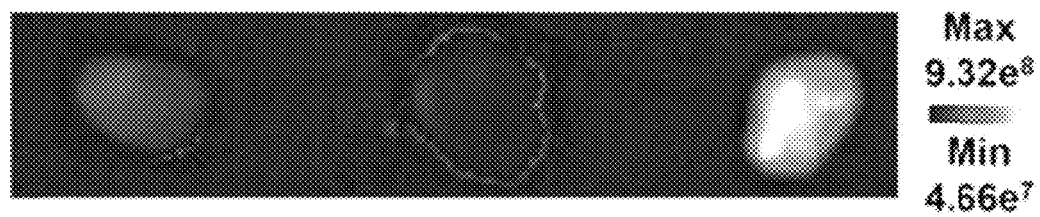
FIG. 3E shows fluorescence images of doxorubicin expressed in tumor tissues excised from tumor animal models after administration of doxorubicin alone (Free DOX), RRG-DOX (SEQ ID NO: 11) of Comparative Example 1, and a drug conjugate (FRRG-DOX) (SEQ ID NO: 7) of Example 1.

FIG. 3E shows fluorescence images of doxorubicin expressed in the tumor tissues excised from the tumor ammal models after administration of doxorublcm alone (Free DOX), RRG-DOX (SEQ ID NO: 11) of Comparative Example 1, and the drug conjugate FRRG-DOX (SEQ ID NO: 7) of Example 1.

Figure 3F:
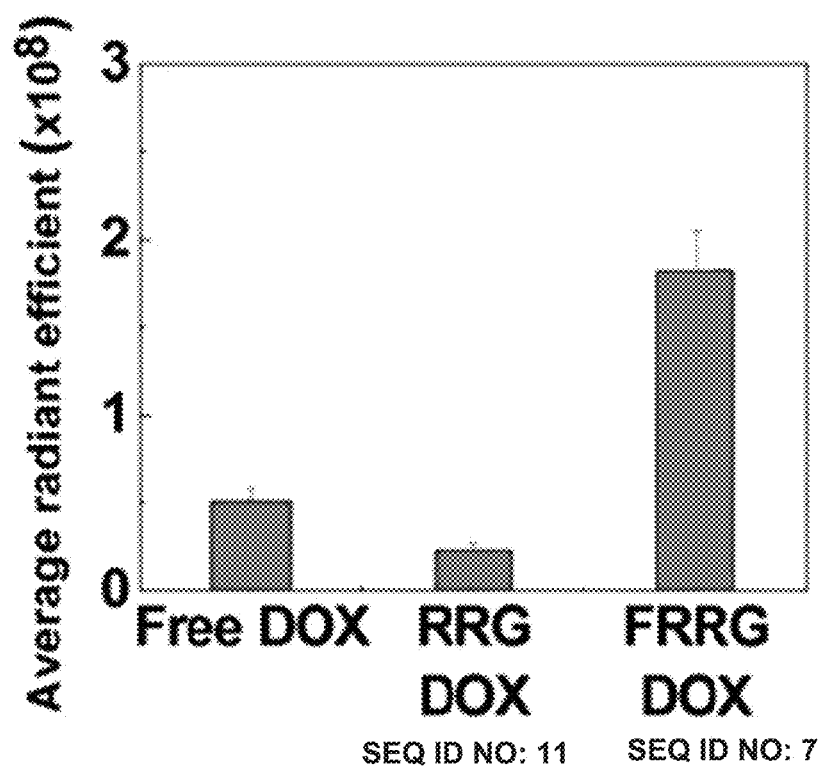
FIG. 3F shows fluorescence intensities from the images of FIG. 3E.

FIG. 3F shows fluorescence intensities from the images of FIG. 3E.

As shown in FIGS. 3D, 3E, and 3F, there were significant differences in the fluorescence intensity of the tumor animal models. Doxorubicin could be specifically expressed in the tumor tissues when FRRG-DOX (SEQ ID NO: 7) of Example 1 was administered not only directly but also intravenously. In addition, targeting of doxorubicin expressed in the tumor tissues enabled effective tumor labeling.

As shown in FIG. 3E, a higher fluorescence intensity was observed in the tumor tissues excised from the animal model after intravenous administration of FRRG-DOX (SEQ ID NO: 7).

In contrast, RRG-DOX (SEQ ID NO: 11) of Comparative Example 1 is structurally similar to FRRG-DOX (SEQ ID NO: 7) of Example 1 but a low fluorescence intensity was observed when treated with RRG-DOX (SEQ ID NO: 11) of Comparative Example 1 compared to when treated with doxorubicin alone. These results reveal that when any one of the amino acids of the peptide of FRRG-DOX (SEQ ID NO: 7) of Example 1 was deleted or altered, no specific activity of FRRG-DOX (SEQ ID NO: 7) against tumor cells was obtained.

In conclusion, specific degradation of FRRG-DOX (SEQ ID NO: 7) by cathepsin B present in tumor tissues leads to the accumulation of the drug (doxorubicin;G-DOX) only in the tumor tissues. In addition, the formation of self-assembled nanoparticles leads to an increase in the concentration of doxorubicin in tumor tissues.

Figure 3G:
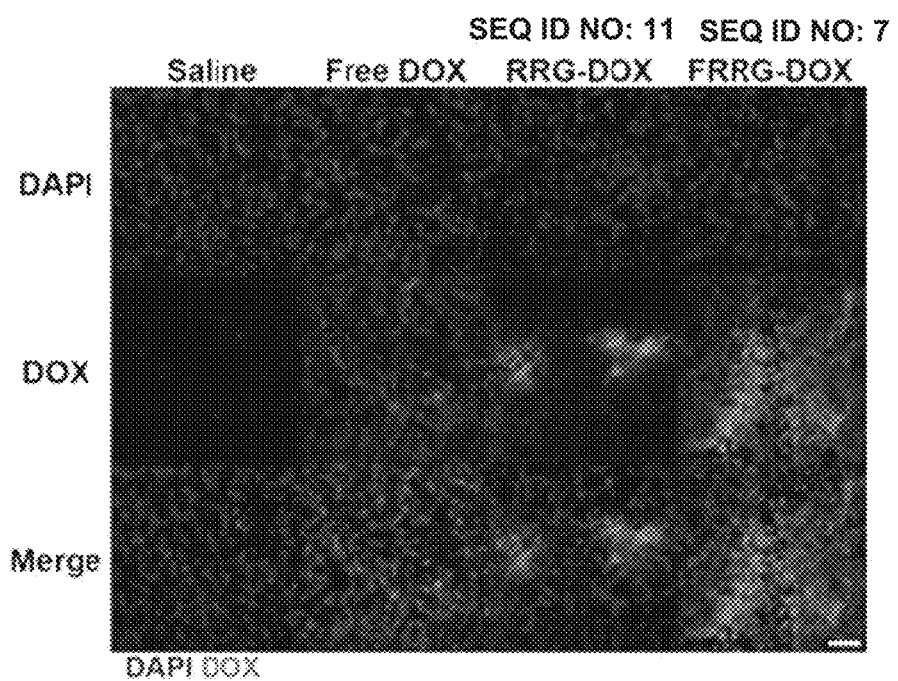
FIG. 3G shows images of DAPI-stained tumor tissues obtained from tumor animal models after administration of doxorubicin alone (Free DOX), RRG-DOX (SEQ ID NO: 11), and the drug conjugate FRRG-DOX (SEQ ID NO: 7), and fluorescence images of doxorubicin (DOX)

FIG. 3G shows images of DAPI-stained tumor tissues obtained from the tumor animal models after administration of doxorubicin alone (Free DOX), RRG-DOX (SEQ ID NO: 11), and the drug conjugate FRRG-DOX (SEQ ID NO: 7), and fluorescence images of doxorubicin (DOX).

As shown in FIG. 3G, FRRG-DOX (SEQ ID NO: 7) of Example 1 was specifically activated in tumor tissues by the EPR effect, with the result that doxorubicin was accumulated in the tumor tissues. In contrast, doxorubicin could not be effectively accumulated in tissues when treated with RRG-DOX (SEQ ID NO: 11) of Comparative Example 1 or doxorubicin alone.

Experimental Example 6: Evaluation of Expression Efficiency of Doxorubicin of FRRG-DOX (SEQ ID NO: 7) Via Intravenous Administration to Tumor Animal Models—2

In this example, the in vivo anticancer effects of doxorubicin (Free DOX) and FRRG-DOX (SEQ ID NO: 7) of Example 1 were investigated. First, $1 \times 10^7$ HT-29 cells were directly injected into the right flank of each tumor animal model constructed in 1) (n=4 per group). When the tumor size reached ~200 mm$^3$, doxorubicin (Free DOX, 5 mg/kg) and FRRG DOX (SEQ ID NO: 7) of Example 1 (5 mg/kg) were administered by tail vein injection once every three days for 15 days.

DPBS (200 μl) was injected into tumor animal model via the tail vein once every three days for 15 days (control).

The therapeutic efficacies of Free DOX, FRRG-DOX (SEQ ID NO: 7), and the control were compared by measuring the tumor volumes (maximum diameter×minimum diameter 2×0.53) for 15 days. The viabilities and weights of the tumor animal models were measured once a day for 15 days. The accumulations of Free DOX and FRRG-DOX (SEQ ID NO: 7) in the tumor tissues of the tumor animal models were monitored using IVIS Lumina Series III (PerkinElmer, Massachusetts, USA). The fluorescence intensities of Free DOX and FRRG-DOX (SEQ ID NO: 7) in the tumor tissues were quantified using the Living Image software (PerkinElmer, Massachusetts, USA).

Figure 4A:
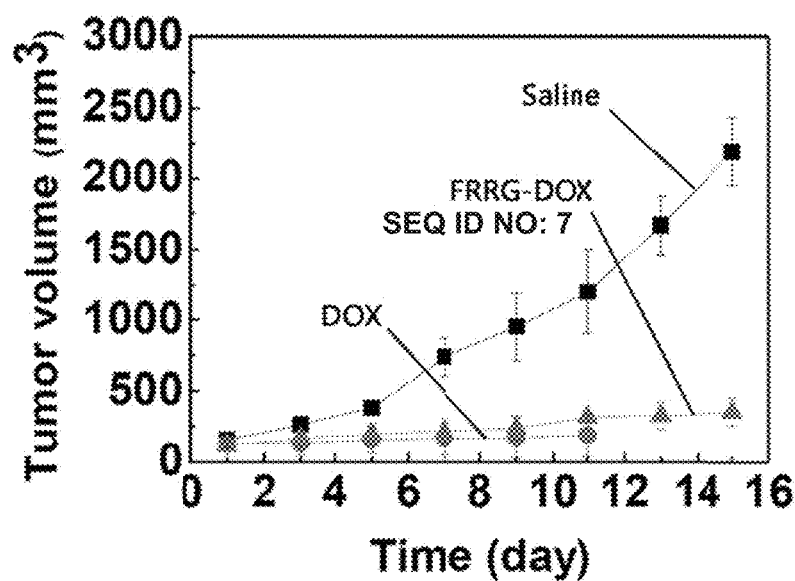
FIG. 4A shows the inhibitory effect of a drug conjugate (FRRG-DOX) (SEQ ID NO: 7) of Example 1 on tumor growth in tumor animal models injected with HT29 tumor, which was analyzed by comparing the tumor volumes ($mm^3$) measured at different time points after administration of doxorubicin alone (DOX) or the drug conjugate FRRG-DOX (SEQ ID NO: 7)
Figure 4B:
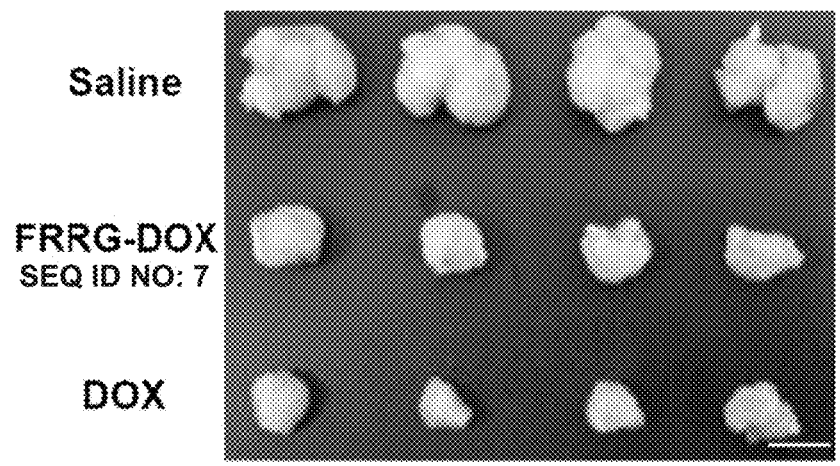
FIG. 4B shows images of tumor tissues excised from tumor animal models injected with HT29 tumor at different time points after administration of doxorubicin alone (DOX) or the drug conjugate FRRG-DOX (SEQ ID NO: 7)

FIG. 4A shows the inhibitory effect of the drug conjugate FRRG-DOX (SEQ ID NO: 7) of Example 1 on tumor growth in the tumor animal models injected with HT29 tumor, which was analyzed by comparing the tumor volumes (mm$^3$) measured at different time points after administration of doxorubicin alone (DOX) or the drug conjugate FRRG-DOX (SEQ ID NO: 7). FIG. 4B shows images of the tumor tissues excised from the tumor animal models injected with HT29 tumor at different time points after administration of doxorubicin alone (DOX) or the drug conjugate FRRG-DOX (SEQ ID NO: 7).

FIGS. 4A and 4B reveal the therapeutic effects and side effects of the drug conjugate FRRG-DOX (SEQ ID NO: 7) in the tumor animal models. As shown in FIGS. 4A and 4B, the administration of doxorubicin alone (Free DOX) and the administration of the drug conjugate FRRG-DOX (SEQ ID NO: 7) were confirmed to significantly inhibit tumor growth. Toxicity to normal cells was observed in the doxorubicin-treated group (Free DOX) whereas no toxicity was observed in the drug conjugate-administered group (FRRG-DOX) (SEQ ID NO: 7).

That is, good inhibitory effects on tumors were observed in the group administered doxorubicin alone and the group administered the drug conjugate FRRG-DOX (SEQ ID NO: 7) of Example 1. The inhibitory effects of doxorubicin and FRRG-DOX (SEQ ID NO: 7) on tumors can be determined as therapeutic effects on cancer in cancer tissues.

Figure 4C:
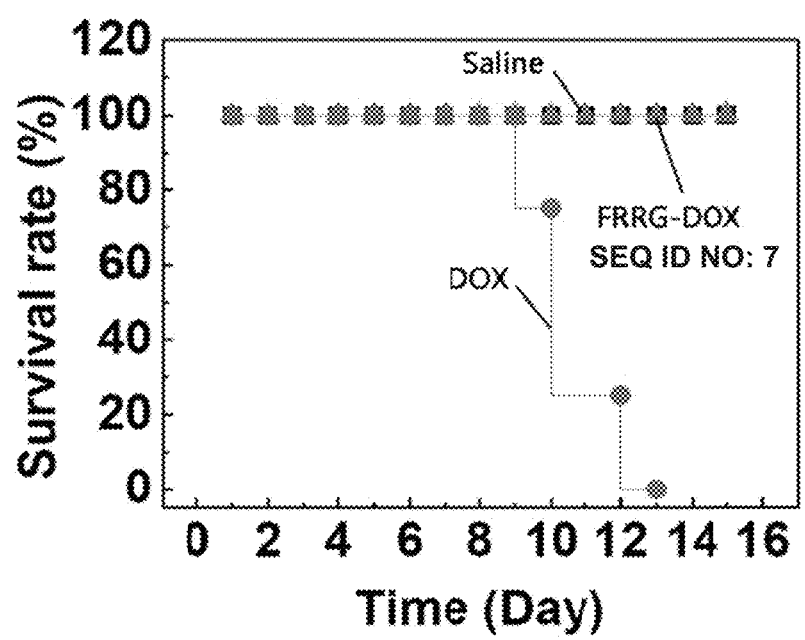
FIG. 4C shows survival rates (%) of tumor animal models injected with HT29 tumor at different time points after administration of doxorubicin alone (DOX) or the drug conjugate FRRG-DOX (SEQ ID NO: 7)

FIG. 4C shows survival rates (%) of the tumor animal models injected with HT29 tumor at different time points after administration of doxorubicin alone (DOX) or the drug conjugate FRRG-DOX (SEQ ID NO: 7).

As shown in FIG. 4C, the weight of the tumor animal models began to decrease after treatment with doxorubicin alone (DOX), and finally their mortality began to increase rapidly due to the toxicity of doxorubicin to normal cells. In contrast, when the drug conjugate FRRG-DOX (SEQ ID NO: 7) of Example 1 was administered, the viability (%) of the animal tumor models was maintained constant at 100% for 16 days. So long as there is not substantially affected by age, it is expected that no death will be caused by tumor disease even after 16 days.

These results lead to the conclusion that since doxorubicin injected in the form of the drug conjugate FRRG-DOX (SEQ ID NO: 7) is activated only in tumor tissues, it inhibits the growth and metastasis of tumor tissues without causing toxicity to normal cells. That is, it is considered that the drug conjugate FRRG-DOX (SEQ ID NO: 7) is substantially free from the side effects of conventional drug carriers or drugs.

Annexin V staining was performed to confirm that apoptosis occurred in tumor tissues excised from the tumor animal models. First, section slides (10 μm) of the excised tumor tissues were washed three times with DPBS, incubated with annexin V solution (200 μl of a binding buffer containing 5 μl of annexin V-Cy5.5) at 37° C. for 20 min, incubated with DAPI at room temperature for 15 min, placed on cover glass, and observed under a confocal laser microscope.

Figure 4D:
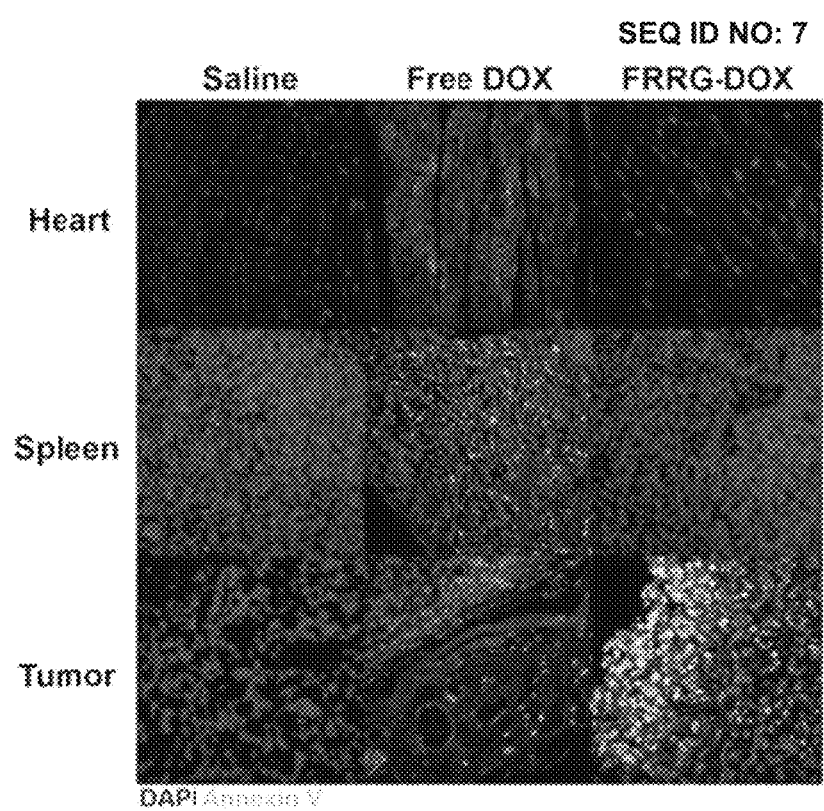
FIG. 4D shows confocal laser microscopy images of organ tissues excised from tumor animal models injected with HT29 tumor after administration of doxorubicin alone (DOX) or the drug conjugate FRRG-DOX (SEQ ID NO: 7), which were measured by annexin V staining to investigate whether apoptosis occurred in the organ tissues. Here, the green colors are annexin V-stained tissues where apoptosis occurred and the blue colors are DAPI-stained cell nuclei.

FIG. 4D shows confocal laser microscopy images of organ tissues excised from the tumor animal models injected with HT29 tumor after administration of doxorubicin alone (DOX) or the drug conjugate FRRG-DOX (SEQ ID NO: 7), which were measured by annexin V staining to investigate whether apoptosis occurred in the organ tissues. In FIG. 4B, the green colors are annexin V-stained tissues where apoptosis occurred and the blue colors are DAPI-stained cell nuclei.

The present invention is aimed at providing a pharmaceutical composition for effectively preventing or treating cancer that inhibits toxicity and side effects encountered with conventional therapeutic agents for cancer, ensuring stability despite long-term administration, and can prevent death caused by secondary side effects upon administration. In view of this, the influences of treatment of the tumor animal models with doxorubicin alone and the drug conjugate FRRG-DOX (SEQ ID NO: 7) of Example 1 on other organs were evaluated, as shown in FIG. 4D.

As shown in FIG. 4D, apoptosis was observed in all of the heart, spleen, and tumor tissues of the tumor animal model administered doxorubicin alone (Free DOX). In contrast, apoptosis was observed only in the tumor tissues of the tumor animal model administered the drug conjugate FRRG-DOX (SEQ ID NO: 7) of Example 1.

Figure 4E:
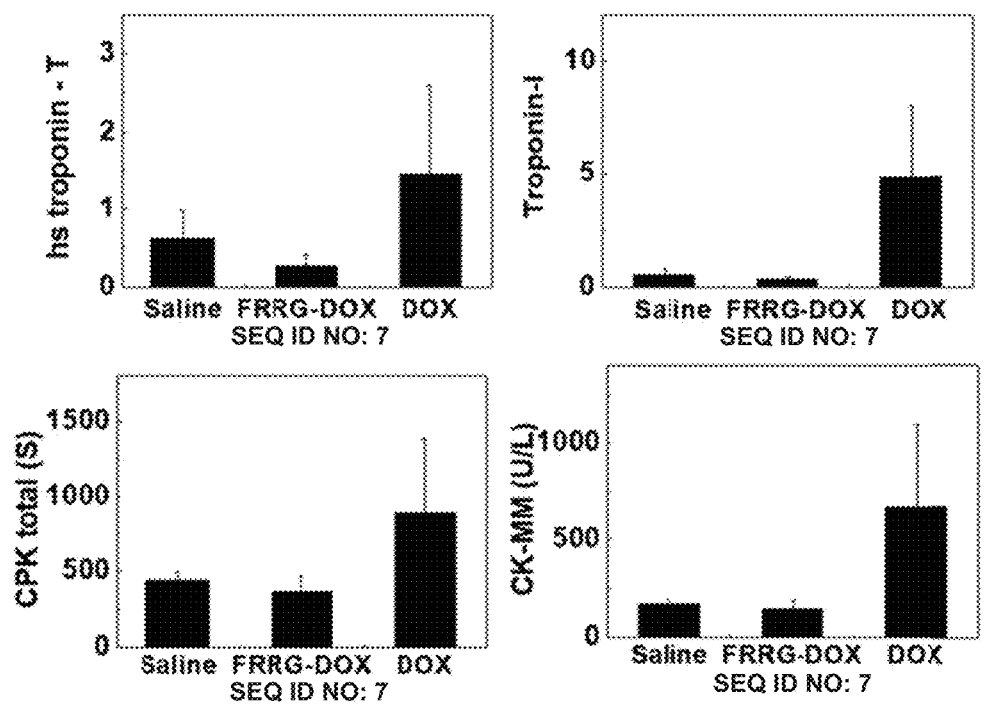
FIG. 4E shows four representative markers indicative of heart damage (including hs troponin-T, Troponin-I, CK-MM, and CPK total) in blood samples from rats as animal models after administration of doxorubicin alone (DOX) or the drug conjugate FRRG-DOX (SEQ ID NO: 7), which were detected to investigate cardiotoxicity in the animal models.

FIG. 4E shows four representative markers indicative of heart damage (including hs troponin-T, Troponin-I, CK-MM, and CPK total) in blood samples from tumor animal models after administration of doxorubicin alone (DOX) or the drug conjugate FRRG-DOX (SEQ ID NO: 7), which were detected to investigate cardiotoxicity in the animal models.

An observation was made as to whether heart damage was caused by administration of doxorubicin alone (DOX) or the drug conjugate FRRG-DOX (SEQ ID NO: 7). As shown in FIG. 4E, higher levels of all markers were observed in the tumor animal model administered doxorubicin alone (Free DOX). In contrast, the levels of the markers indicative of heart damage were observed in the tumor animal model administered the drug conjugate FRRG-DOX (SEQ ID NO: 7) of Example 1 were about two times lower than or comparable to those in the control (saline).

Figure 5A:
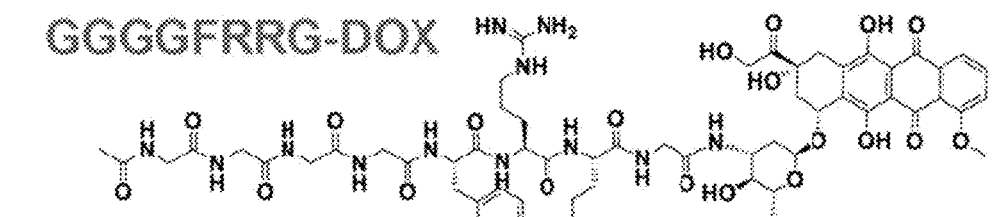
FIG. 5A shows chemical formulae of drug conjugates prepared in Examples 2-4.
Figure 5A:
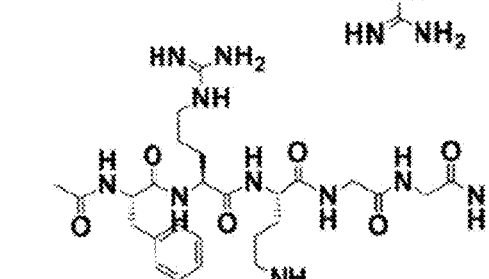

Experimental Example 7: Evaluation of Characteristics and Pharmacological Effects of the Drug Conjugates Prepared in Examples 2-4 in Tumor Animal Models In this example, FRRG DOX (SEQ ID NO: 7) of Example 1 and the drug conjugates of Examples 2-4 having the amino acid sequences similar to that of FRRG DOX (SEQ ID NO: 7) were investigated for their physical properties and anti-tumor effects. FIG. 5A shows chemical formulae of the drug conjugates prepared in Examples 2-4.

Figure 5B:
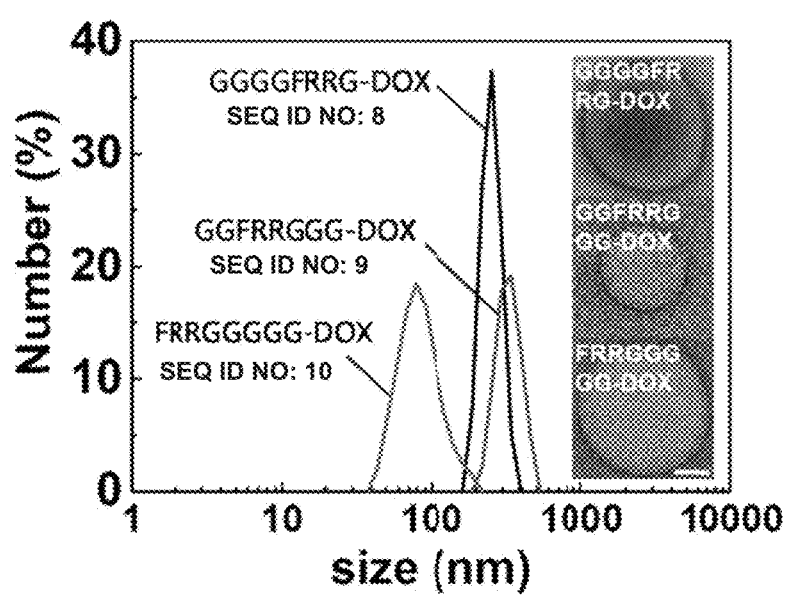
FIG. 5B shows the formation of nanoparticles by the drug conjugates prepared in Examples 2-4 and the measured sizes of the particles.

FIG. 5B shows the formation of nanoparticles by the drug conjugates prepared in Examples 2-4 and the measured sizes of the particles.

As shown in FIG. 5B, GGGGFRRG-DOX (SEQ ID NO: 8) (Example 2), GGFRRGGG-DOX (SEQ ID NO: 9) (Example 3), and FRRGGGGG-DOX (SEQ ID NO: 10) (Example 4) having structures similar to that of FRRG-DOX (SEQ ID NO: 7) of Example 1 formed nanoparticles of different sizes.

Specifically, GGGGFRRG-DOX (SEQ ID NO: 8) (Example 2), GGFRRGGG-DOX (SEQ ID NO: 9) (Example 3), and FRRGGGGG-DOX (SEQ ID NO: 10) (Example 4) were measured to have sizes of 200-600 nm, 50-200 nm, and 300-700 nm, respectively.

Figure 5C:
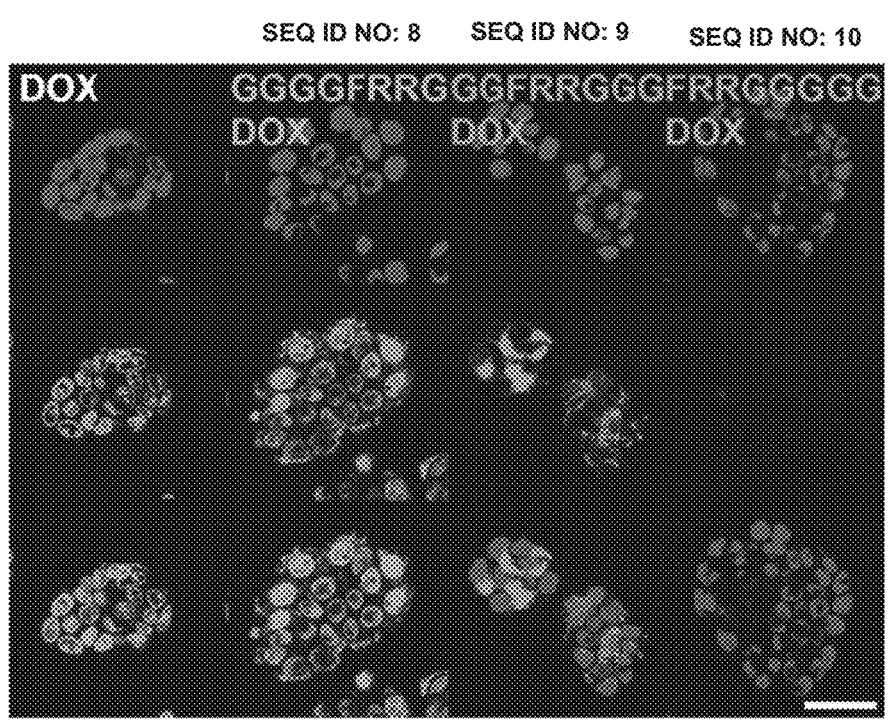
FIG. 5C shows confocal microscopy images of cells treated with doxorubicin (DOX), cells treated with GGGGFRRG-DOX (SEQ ID NO: 8) (Example 2), cells treated with GGFRRGGG-DOX (SEQ ID NO: 9) (Example 3), and cells treated with FRRGGGGG-DOX (SEQ ID NO: 10) (Example 4)
Figure 5D:
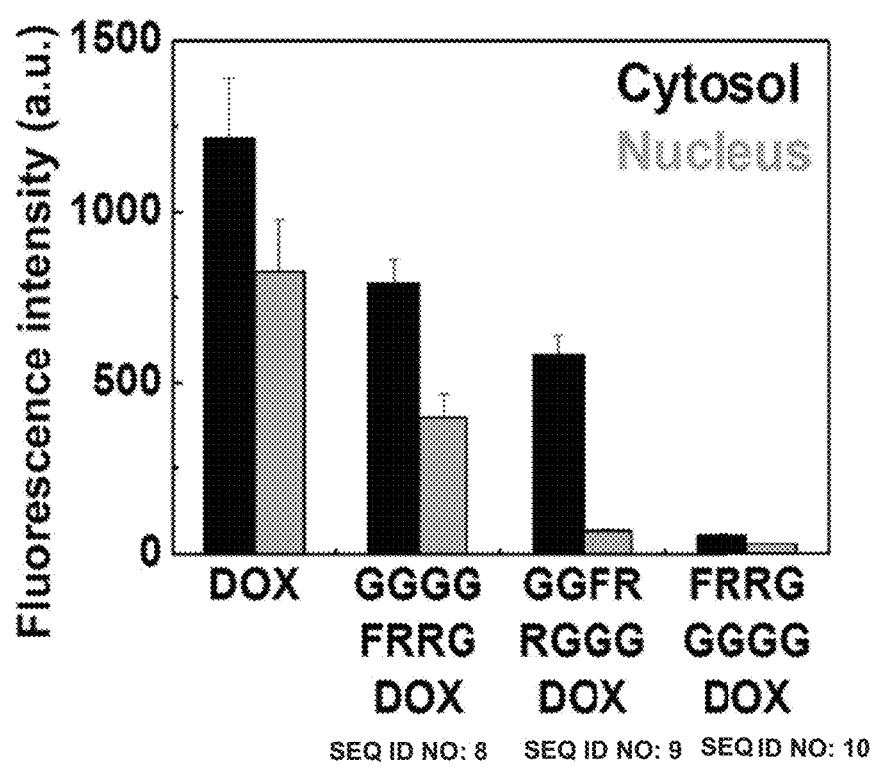
FIG. 5D shows fluorescence intensities from the images of FIG. 5C. Here, "Cytosol "and "Nucleus" indicate the fluorescence intensities of DOX measured in cytosol and cell nuclei, respectively.

FIG. 5C shows confocal microscopy images of cells treated with doxorubicin (DOX), cells treated with GGGGFRRG-DOX (SEQ ID NO: 8) (Example 2), cells treated with GGFRRGGG-DOX (SEQ ID NO: 9) (Example 3), and cells treated with FRRGGGGG-DOX (SEQ ID NO: 10) (Example 4). FIG. 5D shows fluorescence intensities from the images of FIG. 5C. In FIG. 5D, "Cytosol "and "Nucleus" indicate the fluorescence intensities of DOX measured in cytosol and cell nuclei, respectively.

As shown in FIGS. 5C and 5D, GGGGFRRG-DOX (SEQ ID NO: 8) (Example 2), GGFRRGGG-DOX (SEQ ID NO: 9) (Example 3), and FRRGGGGG-DOX (SEQ ID NO: 10) (Example 4) showed antitumor effects or intracellular uptake effects.

Specifically, FRRGGGGG-DOX (SEQ ID NO: 10) (Example 4) whose sequence consists of four or more consecutive glycine (G) residues located downstream of FRR (SEQ ID NO: 6) was not readily absorbed into cells, which explains why the use of FRRG-DOX (SEQ ID NO: 7) (Example 1), GGGGFRRG-DOX (SEQ ID NO: 8) (Example 2) or GGFRRGGG-DOX (SEQ ID NO: 9) (Example 3) is preferred.

GGFRRGGG-DOX (SEQ ID NO: 9) (Example 3) whose sequence consists of three consecutive glycine (G) residues located downstream of FRR (SEQ ID NO: 6) was readily absorbed into cells but its uptake into cell nuclei was 10 times lower than those of the drug conjugates of Examples 1 and 2, which explains why the use of FRRG-DOX (SEQ ID NO: 7) (Example 1) or GGGGFRRG-DOX (SEQ ID NO: 8) (Example 2) is most preferred.

Figure 5E:
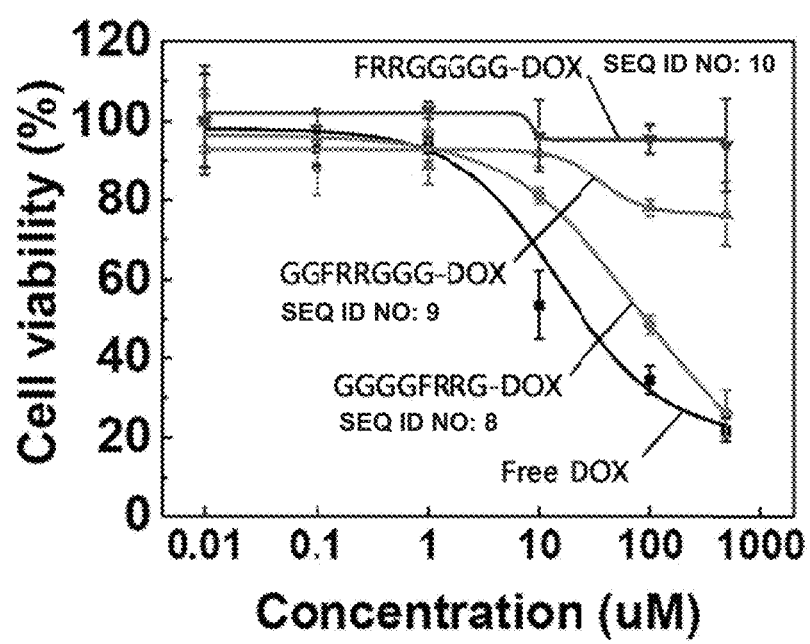
FIG. 5E shows cell viabilities (%) of tumor cells (HT29) after treatment with doxorubicin (DOX), GGGGFRRG-DOX (SEQ ID NO: 8) (Example 2), GGFRRGGG-DOX (SEQ ID NO: 9) (Example 3) or FRRGGGGG-DOX (SEQ ID NO: 10) (Example 4)

FIG. 5E shows cell viabilities (%) of tumor cells (HT29) after treatment with doxorubicin (DOX), GGGGFRRG-DOX (SEQ ID NO: 8) (Example 2), GGFRRGGG-DOX (SEQ ID NO: 9) (Example 3), and FRRGGGGG-DOX (SEQ ID NO: 10) (Example 4).

FRRGGGGG-DOX (SEQ ID NO: 10) (Example 4) was not readily absorbed into cells due to the presence of many amino acids bound to the hydrophilic amino acid phenylalanine (F). Accordingly, it is preferred that n in Formula 1 representing the amphiphilic peptide of the inventive drug conjugate is greater than 1.

GGGGFRRG-DOX (SEQ ID NO: 8) (Example 2) was confirmed to show the same antitumor effect as DOX. FRRG-DOX (SEQ ID NO: 7) (Example 1) and GGGGFRRG-DOX (SEQ ID NO: 8) (Example 2) were most effective in antitumor action.

Figure 5F:
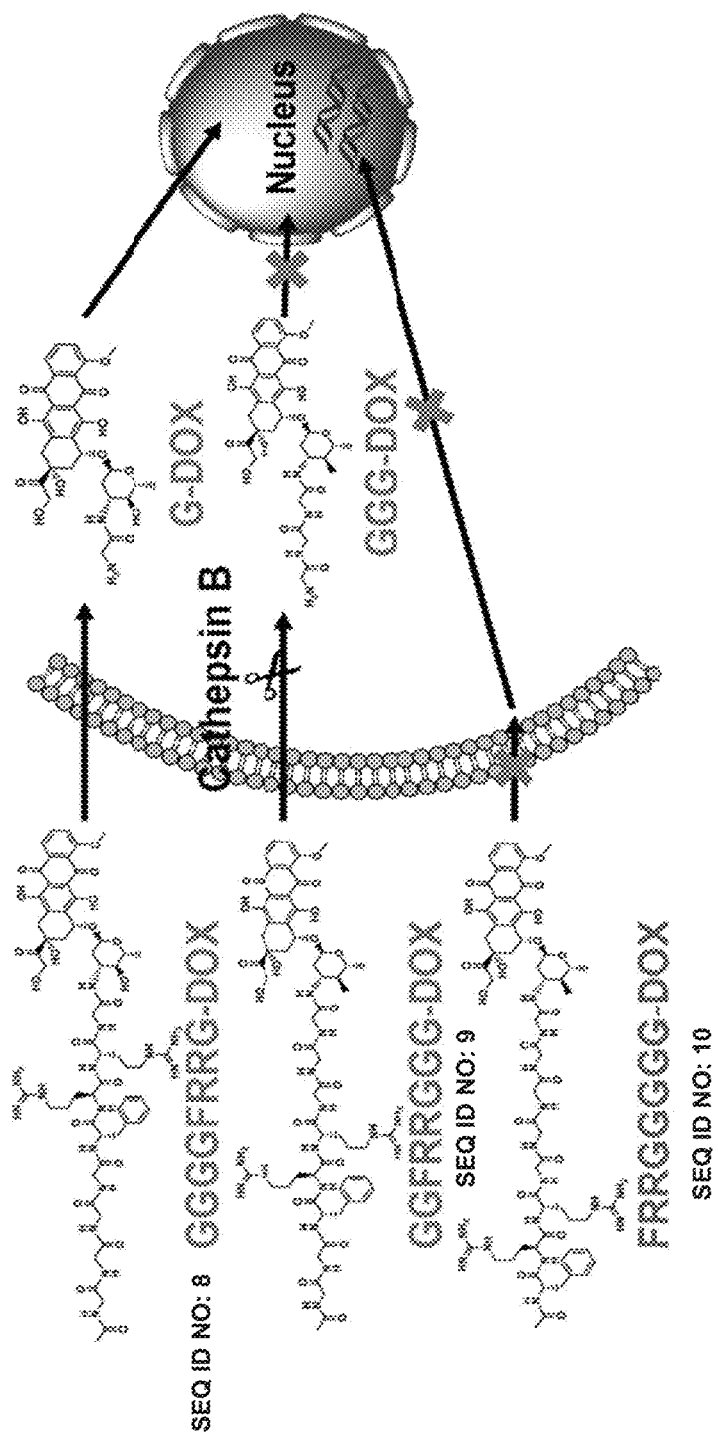
FIG. 5F shows intracellular uptake pathways of the drug conjugates GGGGFRRG-DOX (SEQ ID NO: 8) (Example 2), GGFRRGGG-DOX (SEQ ID NO: 9) (Example 3), and FRRGGGGG-DOX (SEQ ID NO: 10) (Example 4), which were obtained from the experimental results of FIGS. 5B to 5E.

FIG. 5F shows intracellular uptake pathways of the drug conjugates GGGGFRRG-DOX (SEQ ID NO: 8) (Example 2), GGFRRGGG-DOX (SEQ ID NO: 9) (Example 3), and FRRGGGGG-DOX (SEQ ID NO: 10) (Example 4), which were obtained from the experimental results of FIGS. 5B to 5E.

Experimental Example 8: Evaluation of Characteristics and Pharmacological Effects of the Drug Conjugates Prepared in Examples 2-4 in Tumor Animal Models 1) Multi-Electrode Array (MEA) Analysis Multi-electrode array analysis was conducted by the following procedure. First, human induced pluripotent stem cell-derived cardiomyocytes (hiPSC-CMs, Cellular Dynamics International [CDI], Madison, Wis., USA) were thawed in a 100 mm culture dish. After 1 week, the thawed hiPSC-CMs were plated in an MEA plate coated with fibronectin solution (50 μg/ml). On day 2 after thawing, the plating medium was replaced with a maintenance medium (CDI). Maintenance media were replaced with new ones every 2-3 days. Only 50% of the culture media were replaced with new ones. 2 weeks after plating in the plate, field potentials of spontaneously beating cardiomyocytes were recorded using a Maestro system (Axion Biosystems Inc., Atlanta, Ga., USA). The waveforms of the extracellular field potentials were recorded 10 min after the equilibration period. Inter-spike interval and extracellular field potential duration (FPD) were analyzed and quantified. To minimize the influence of the beat rate on FPD, corrected FPD (FPDcF) was calculated using Fridericia's formula 1:

$$FPDcF = FPD/[\text{inter-spike interval}]1/3 \qquad (1)$$

2) Electrocardiography (ECG) Analysis

ECG analysis was performed under the approval of the Institutional Animal Care and Use Committee at the Korea Institute of Toxicology. All procedures were performed according to the National Institutes of Health guidelines for the care and use of laboratory animals. A mixture of isoflourane and oxygen as an anaesthetic gas was injected at a rate of 2 cc/min to ICR mice (25-35 g, Orient Bio Inc., Seoul, Korea). ECG was measured before injection of the anaesthetic gas into an animal bio amp (ADinstruments Pty Ltd, Bella Vista, Australia). The measured ECG was defined as baseline. For 6 h after injection of the anaesthetic gas, ECG was measured. All mice were injected intravenously with saline, 5 mg/kg doxorubicin (in saline) or 10 mg/kg FRRG-doxorubicin (SEQ ID NO: 7) (Example 1) (in saline). The measured ECG data were analyzed using the LabChart 8 software (ADinstruments Pty Ltd, Bella Vista, Australia). Corrected QT (QTc) was calculated using Van de Water's formula 2 and Bazett's formula 3:

$$QTc\text{-}V = 0.087[(60/HR)-1] \qquad (2)$$

$$QTc\text{-}B = QT/(RR)1/2 \qquad (3)$$

3) Results of Analysis for Electrocardiogram-Related Toxicity

Figure 6A:
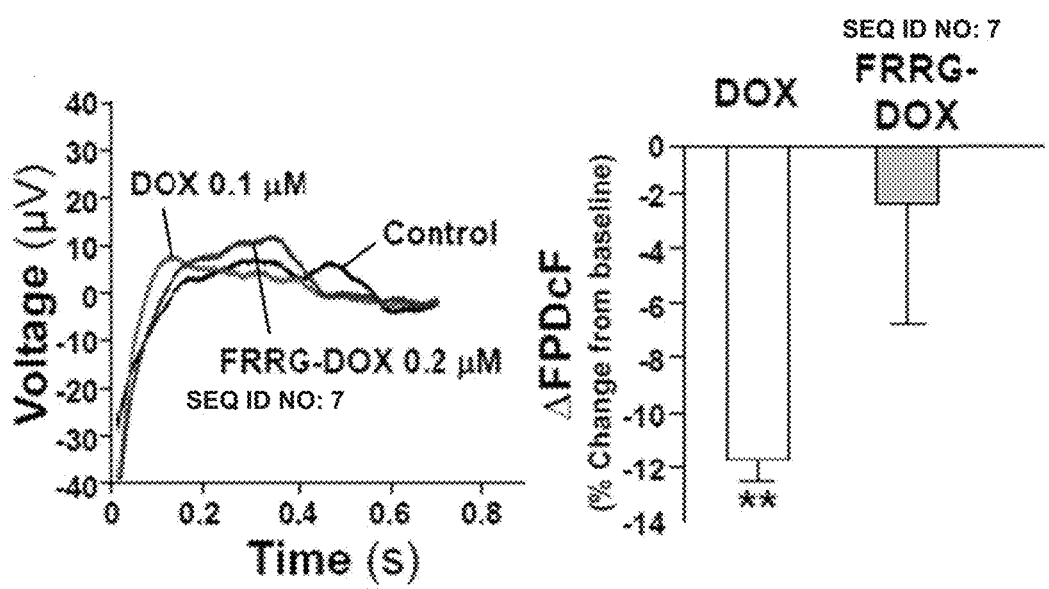
FIG. 6A shows the results of multi-electrode array (MEA) analysis for hiPSC-CMs treated with FRRG-DOX (SEQ ID NO: 7) (Example 1) (0.2 µM) and doxorubicin (0.1 µM)

FIG. 6A shows the results of multi-electrode array (MEA) analysis for hiPSC-CMs treated with FRRG-DOX (SEQ ID NO: 7) (Example 1) (0.2 μM) and doxorubicin (0.1 μM).

As shown in FIG. 6A, the FPD and FPDcF of hiPSC-CMs treated with doxorubicin alone were significantly low compared to the baseline whereas those of hiPSC-CMs treated with FRRG-DOX (SEQ ID NO: 7) (Example 1) remained substantially unchanged. That is, cardiotoxicity was significantly reduced when FRRG-DOX (SEQ ID NO: 7) (Example 1) was used compared to when doxorubicin was directly used.

Figure 6B:
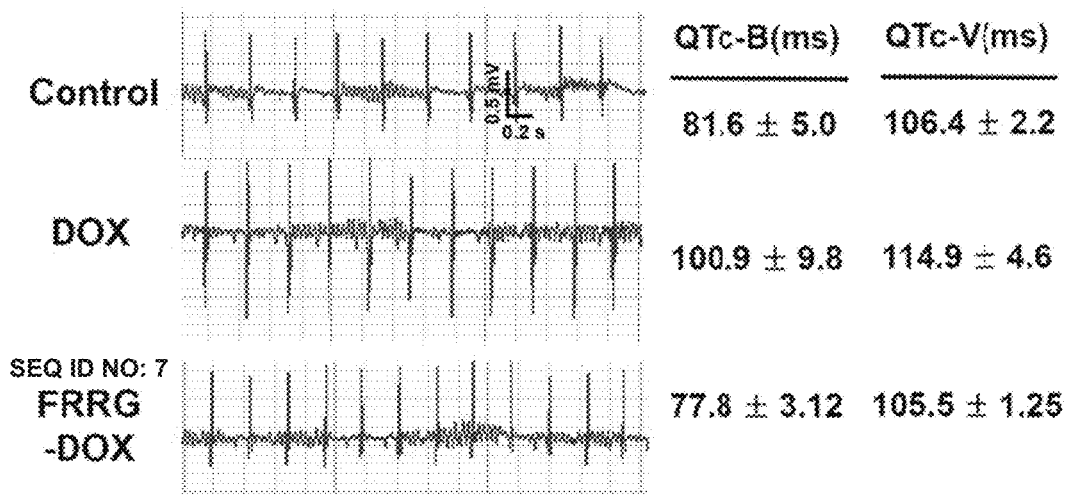
FIG. 6B shows electrocardiograms of ICR mice treated with FRRG-DOX (SEQ ID NO: 7) (Example 1) and doxorubicin.

FIG. 6B shows electrocardiograms of ICR mice treated with FRRG-DOX (SEQ ID NO: 7) (Example 1) and doxorubicin.

As shown in FIG. 6B, QTc values measured in the ICR mice treated with 5 mg/kg of doxorubicin were extended compared to those measured in the control. In contrast, QTc values measured in the ICR mice treated with FRRG-DOX (SEQ ID NO: 7) (Example 1) were detected to be similar to those measured in the control. In conclusion, since the drug conjugate FRRG-DOX (SEQ ID NO: 7) (Example 1) is activated only in the tumor sites of the experimental animals, it causes no toxicity to normal organs, including heart, liver, kidney, and spleen.

To conclude, the drug conjugate FRRG-DOX (SEQ ID NO: 7) showed a tumor-specific prophylactic or therapeutic effect, which was demonstrated through the animal experiments. In addition, the drug conjugate FRRG-DOX (SEQ ID NO: 7) was confirmed to be a stable drug without causing toxicity to other organ tissues and even life. Furthermore, the drug conjugate FRRG-DOX (SEQ ID NO: 7) could be prepared in a very simple manner, thus being advantageous from an economic viewpoint.

What is claimed is:

1. A low molecular weight drug conjugate, consisting of:
    an amphiphilic peptide having the sequence set forth in any one of SEQ ID NOS: 1 to 4; and
    a hydrophobic drug,
    wherein the amphiphilic peptide is directly conjugated to the hydrophobic drug without a linker,
    wherein the hydrophobic drug is selected from the group consisting of taxol, bendamustine, busulfan, carmustine, chlorambucil, cyclophosphamide, dacarbazine, adriamycin, daunomycin, ifosfamide, melphalan, procarbazine, streptozocin, temozolomide, asparaginase, capecitabine, cytarabine, 5-fluorouracil, fludarabine, gemcitabine, methotrexate, pemetrexed, raltitrexed, actinomycin-D, bleomycin, daunorubicin, doxorubicin, pegylated liposomal doxorubicin, epirubicin, idarubicin, mitomycin, mitoxantrone, etoposide, docetaxel, irinotecan, paclitaxel, topotecan, vinblastine, vincristine, vinorelbine, carboplatin, cisplatin, oxaliplatin, alemtuzumab, BCG, bevacizumab, cetuximab, denosumab, erlotinib, gefitinib, imatinib, interferon, ipilimumab, lapatinib, panitumumab, rituximab, sunitinib, sorafenib, temsirolimus, trastuzumab, clodronate, ibandronic acid, pamidronate, and zoledronic acid, and
    wherein the conjugate is cleavable by cathepsin B to release the hydrophobic drug.

2. The drug conjugate according to claim 1, wherein the drug conjugate has a molecular weight of 800 to 3000 Da.

3. Spherical self-assembled nanoparticles spontaneously formed by the drug conjugate according to claim 1 in a solvent and having a structure in which hydrophobic moieties of the drug conjugate form a core and hydrophilic moieties of the drug conjugate are exposed to the outside of the core.

4. The self-assembled nanoparticles according to claim 3, wherein the solvent is selected from the group consisting of distilled water, phosphate buffered solution (PBS), physiological saline, distilled water containing 0.5 to 1% NaCl, and phosphate buffered solution (PBS) containing 0.5 to 1% NaCl.

5. The self-assembled nanoparticles according to claim 3, wherein the self-assembled nanoparticles have an average diameter of 50 to 500 nm.

* * * * *